United States Patent [19]

Johnson et al.

[11] Patent Number: 5,795,756
[45] Date of Patent: Aug. 18, 1998

[54] METHOD AND COMPOUNDS FOR THE INHIBITION OF ADENYLYL CYCLASE

[76] Inventors: Roger A. Johnson, 7 Bayview Ave., East Setauket, N.Y. 11733; Laurent Désaubry, 15 Beaverdale La., Stony Brook, N.Y. 11790; Ilana Shoshani, 27 Artisen Ave., Huntington, N.Y. 11743

[21] Appl. No.: 762,833

[22] Filed: Dec. 10, 1996

Related U.S. Application Data

[60] Provisional application No. 60/008,507 Dec. 11, 1995.

[51] Int. Cl.$^6$ .............................. C12N 9/00; C07H 19/20
[52] U.S. Cl. .................. 435/183; 536/26.21; 536/26.23; 536/26.26; 536/26.7; 544/264
[58] Field of Search ........................... 536/26.21, 26.23, 536/26.26, 26.7; 544/264; 435/183

[56] References Cited

U.S. PATENT DOCUMENTS 3,910,885  10/1975  Moffatt et al. .................. 536/27.23
5,449,664  9/1995   Verheyden et al. .................. 514/45

OTHER PUBLICATIONS

Johnson et al., "Isozyme–Dependent Sensitivity of Adenylyl Cyclases to P–Site–Mediated Inhibition by Adenine Nucleotides and Nucleoside 3'–Polyphosphates," *J. Biol. Chem.*, 272(14), 8962–8966 (Apr. 4, 1997).

Désaubry et al.(I), "Conjugation of Nucleoside Triphosphates to an Amino Linker." *Bioorganic & Medicinal Chem. Letters*, 7(2), 123–126 (Jan. 21, 1997).

Désaubry et al.(II), "Inhibition of Adenylyl Cyclase by a Family of Newly Synthesized Adenine Nucleoside 3'–Polyphosphates," *J. Biol. Chem.*, 271(24), 14028–14034 (Jun. 14, 1996).

Désaubry et al.(III), "2', 5'–Dideoxyadenosine 3'–Polyphosphates Are Potent Inhibitiors of Adenylyl Cyclases," *J. Biol. Chem.*, 271(5), 2380–2382 (Feb. 2, 1996).

Désaubry et al.(IV), "Synthesis of 2', 5'–Dideoxy–Adenosine–3+–Monophosphate Derivatives as Allosteric Inhibitors of Adenylyl Cyclase," *Nucleosides & Nucleotides*, 14(6), 1453–1460 (Aug. 1995).

Nakajima et al., "Facile and Selective Synthesis of Diadenosine Polyphosphates Through Catalysis of Leucyl–t–RNA Synthetase Coupled with ATP Regeneration," *Agric. Biol. Chem.*, 53(3), 615–623 (1989); *Chem. Abstracts*, 111(21), p. 408, Abstr. No. 190876w (Nov. 20, 1989); only Abstract supplied.

Cullis et al., "The Reactivity of Adenosine 5'–O–(S–methyl–1–thiotriphosphate): A Facile Way of Generating cyclo–Diphosphate Dianion," *J. Chem. Soc.: Chem. Communications, Issue No. 2*, 106–108 (Jan. 1989).

Jankowska et al., "Chemical Synthesis of 5'–Phosphorylated DNA Fragments and Their Constituents," *Bull. Pol. Acad. Sci.*, 31(1–2), 17–22 (1983); *Chem. Abstracts*, 101(1), pp. 654–655, Abstract No. 7588k (Jul. 2, 1984); only Abstract supplied.

Kozarich et al., "Ribonucleoside 3'–Di–and –Triphosphates. Synthesis of Guanosine Tetraphosphate (ppGpp)," *Biochemistry*, 14(5), 981–988 (Mar. 11, 1975).

Etaix et al., "Phopsphorylation of Nucleosides in Aqueous Solution Using Trimetaphosphate: Formation of Nucleoside Triphosphates," *J. Carbohydrates, Nucleosides, Nucleotides*, 5(2), 91–110 (1978); *Chem. Abstracts*, 89, p. 638, Abstract No. 180281m (1978); only Abstract supplied.

Malevskii et al., "Charge–Transfer Complexes of Nucleic Acid Nitrogen Bases and Their Analogs with Benzoquinone. Evidence of II–Donor Character," *Mol. Biol. (Moscow)*, 15(2), 447–453 (1981); *Chem. Abstracts*, 94(25), pp. 176–177, Abstract No. 204014h (Jun. 22, 1981).

Holy et al., "Oligonucleotide Compounds. XXIX. Reactions of Ribonucleoside 2'(3')–Phosphates With Dimethylformamide Acetals," *Coll. Czech. Chem. Comm.*, 34(1), 253–271 (1989).

Hecht et al., "Hydrolysis of Ribonucleoside 3'–Diphosphates by Rye Grass 3'–Nucleotidase," *Biochemistry*, 14(5), 974–981 (Mar. 11, 1975).

Englund et al., "Enzymatic Synthesis of Deoxyribonucleic Acid," *J. Biological Chem.*, 244(11), 3038–3044 (Jun. 10, 1969).

Mitchel et al., "The Synthesis and Properties of Adenosine–2'–diphosphate and Adenosine–3'–diphosphate," *Canadian J. Biochemistry*, 45(1), 89–99 (1967); *Chem. Abstracts*, 66(9), p. 3307, Abstract No. 34846h (Feb. 27, 1967); only Abstract supplied.

Josse et al., "Syntheses of Deoxynucleoside 3'–Triphosphates," *Biochemistry*, 4(12),2825–2831 (Dec. 1965).

R. A. Johnson et al. (I), "Cation and Structural Requirements for P Site–Mediated Inhibition of Adenylate Cyclase," *Molecular Pharmacology*, 35, 681–688 (1989).

L. Désaubry et al., "Synthesis of 2'–Deoxy–and 2', 5'–Dideoxy–Adenosine–3'–Di–and 3'–Triphosphate," *Tetrahedron Letters*, 36(7), 995–996 (1995).

R. A. Johnson et al. (II), "Adenylyl Cyclase 'P'–Site Inhibitors Induce Differentiation in ob–1771 Pre–Adipocytes," Abstract, XII Intl. Congr. of Pharmacology, Montreal, Canada, Jul. 24–27, 1994, *Can. J. Physiology Pharmacology*, 72(Suppl. 1), 511 (1994).

R. A. Johnson et al., "Potent New Inhibitors of Adenylyl Cyclases Point to New Regulatory Pathways," Amer. Soc. Cell Biol. 1994 Mtg., San Francisco, CA, Abstract No. 65, *Molecular Biology of the Cell*, 5(10, Supplement), p. 12a (Dec. 10–14, 1994).

*Primary Examiner*—John Kight
*Assistant Examiner*—L. Eric Crane
*Attorney, Agent, or Firm*—Bell, Boyd & Lloyd

[57] ABSTRACT

The present invention reveals a new series of derivatives and analogues of adenine and adenosine, i.e., 3'-adenosine derivatives, which inhibit adenylyl cyclase activity. These newly synthesized compounds include the most potent inhibitors of adenylyl cyclases known. The present invention also discloses a method for measuring the inhibition of adenylyl cyclase activity.

22 Claims, No Drawings

5,795,756

METHOD AND COMPOUNDS FOR THE INHIBITION OF ADENYLYL CYCLASE

This patent application was supported in part by a grant from the U.S. Government, National Institutes of Health DK 38828. The U.S. Government may have certain rights in the invention.

This patent application claim benefit under 35 USC Section 119(e) of any U.S. Pat. No. 60/008,507 filed Dec. 11, 1996.

BACKGROUND OF THE INVENTION

1. FIELD OF THE INVENTION

The present invention discloses a new series of derivatives of adenine and adenosine, which inhibit adenylyl cyclase activity. These newly synthesized compounds include the most potent in vitro inhibitors of adenylyl cyclases known. The present invention also discloses a method for measuring the inhibition of adenylyl cyclase activity.

2. DESCRIPTION OF THE RELATED ART

Adenosine-3':5'-cyclic monophosphate (cAMP) is the second messenger involved in signal transduction for numerous neurotransmitters and hormones[1]. The cAMP pathway can be regulated pharmacologically by many drugs that are of particular value in the treatment of many diseases, and therefore there is much current interest in identifying new agents acting on this pathway. Regulation of this pathway can be achieved through changes in the activities of cAMP-phosphodiesterases[2], cAMP-dependent protein kinases[3], or adenylyl cyclases[1].

Adenylyl cyclases are a family of enzymes that:

a) catalyze the formation of cAMP from adenosine-5'-triphosphate (5'ATP);

b) mediate the physiological effects of numerous hormones and neurotransmitters; and c) belong to a super family of membrane-bound transporters and channel proteins.

Numerous drugs have been developed as therapeutic agents that inhibit cyclic nucleotide phosphodiesterases[4], the effects of which are to raise cellular cAMP levels in tissues and organs on which they act. For example, theophylline, an inhibitor of all isozyme families of phosphodiesterases, is used clinically to treat asthmas[5]. Rolipram, an inhibitor of type IV phosphodiesterase, is used in the treatment of depressions[6]. And several inhibitors of type III phosphodiesterase have been used clinically to treat patients with moderate to severe heart failure. These latter drugs enhance cardiac index without elevating mean arterial blood pressure and lowering systemic vascular resistance[4] and hence, have significant advantages over β-agonists and digitalis.

However, drugs that act directly on adenylyl cyclases have been less well explored, although agents which indirectly activate or indirectly inhibit the enzyme are commonly used in the treatment of disease. For example, drugs of the class β-blockers are commonly used to treat hypertension and these act to inhibit adenylyl cyclase indirectly by blocking the stimulatory effects of the sympathetic nervous system to activate adenylyl cyclase in the heart, thereby reducing cardiac output[7]. Thus, agents that reduce adenylyl cyclase activity directly can have a similar cardiac-sparing effect and reduced cardiomyopathy and heart failure. Adenylyl cyclases are potently and directly inhibited by analogues of adenosine, via a specific domain[8]. This binding domain is referred to as the "P"-site from an evident requirement for an intact purine moiety[9]. The essential features include the following:

a) inhibition is non-competitive with respect to substrate[9–16], consistent with and corroborated by a number of other studies indicating that inhibition is at a site distinct from catalysis[17];

b) potencies of "P"-site inhibitory ligands are substantially greater with stimulated forms of adenylyl cyclase than with the basal enzyme [12–14,16–21];

c) potency of inhibition is isozyme-dependent[21,22], suggesting the possibility that the physiological importance of this inhibitory mechanism is dictated by the isozyme expressed in a given tissue;

d) inhibition has a striking requirement for an intact adenine moiety in that inosine, guanosine, cytosine, thymidine, and uridine are inactive, and for adenosine $N^6$-and C(8)-substitutions are not tolerated, N(3)-, N(7)-, and N(9)-deaza analogues are inactive[19], though 2-fluoroadenosine and 2-fluoro-2'-deoxyadenosine are inhibitory[23];

e) inhibition exhibits a strong preference for 3'-phosphate, but not cyclic phosphates (3':5'or 2':3')[11,19];

f) 2'-deoxy- and especially 2', 5'-dideoxy-ribosyl compounds[9,10,13,19,22,24] exhibit enhanced inhibitory potency; and g) there is tolerance for significant modifications of the ribose moiety, especially tolerance for large substitutions at the 3'-position, as evidenced particularly by the inhibitory effectiveness of 2'-deoxy-adenosine-dinucleotides and 2'-deoxyadenosine-penta-nucleotides, 3'-(4-fluorosulfonylbenzoyl) -2', 5'-dideoxyadenosine (2', 5'-dd-3' FSB-Ado)[17,19], and 3'-succinyl-2', 5'-dideoxyadenosine[19].

Tolerated modifications to or replacements of the ribosyl moiety include: 9-β-D-arabinofuranosyl-adenine ($IC_{50}$ ~100 µM), 9-β-D-xylofuranosyl-adenine ($IC_{50}$ ~25 µM)[9]; eritadenine ($IC_{50}$ ~6–12 µM)[24]; 9- (tetrahydro-5-methyl-2-furyl)-adenine ($IC_{50}$ ~8 µM), 9-(tetrahydro-2-furyl)-adenine ($IC_{50}$ ~10 µM), 9-cyclopentyl-adenine ($IC_{50}$ ~20 µM), and 9-furfuryl-adenine ($IC_{50}$ ~26 kM)[10].

In this patent application, we describe the synthesis of a new series of analogues and derivatives of adenine and of adenosine, which interact with the "P"-site specific binding domain on adenylyl cyclases. In general, these newly synthesized compounds include the most potent inhibitors of adenylyl cyclases known and are more potent than hormones whose effects must be mediated by G-proteins.

The synthesis of 3'-nucleotides has received considerably less attention than has the synthesis of the corresponding 5'-polyphosphates since the former are more difficult to synthesize and as their biological role is not as well described[25–33]. The only similar nucleotides are the Magic Spots, which are naturally occurring guanosine derivatives polyphosphorylated in both 3'- and 5'-positions[34–38].

The adenine derivatives of the present invention inhibit adenylyl cyclases directly. The cell permeable variants, e.g. 9-(cyclopentyl)-2-fluoroadenine, inhibit the enzyme in intact cells and tissues and one such P-site inhibitor, 2', 5'-dideoxy-adenosine has been used to counteract the effects of cholera intoxication in intestinal epithelium[39]. In addition, the cell impermeable variants, e.g. the adenine nucleoside 3'-polyphosphates, inhibit adenylyl cyclase when microinjected into cells or when introduced into cells by the application of liposome technology.

The compounds of the present invention are also useful in the preparation of covalent affinity probes and affinity chromatography matrices. Moreover, members of this new class of drug are important to many aspects of biology, biochemistry, pharmacology, and therapeutics and will find use in the treatment of various diseases and, more specifically, treatment of cardiovascular diseases.

SUMMARY OF THE INVENTION

The present invention discloses a new class of analogues and derivatives of adenine and adenosine, i.e., 3'-adenosine derivatives, which include the most potent in vitro inhibitors of adenylyl cyclases known and are more potent than hormones whose effects must be mediated by G-proteins. More specifically, the present invention discloses the synthesis of the following new compounds, the numbers for which are also the compound numbers used throughout the syntheses described below:

1). 2', 5'-dideoxyadenosine-3'-[2-([(5-dimethylamino-1-naphthalenesulfonamido) -(N-methyl)]-aminoethyl)-phosphate];
2). 2', 5'dideoxyadenosine-3'-[(3-cholesteryl)-phosphate];
3). 2', 5'-dideoxyadenosine-3'-diphosphate;
4). 2', 5'-dideoxyadenosine-3'-triphosphate;
5). 2', 5'-dideoxyadenosine-3'-tetraphosphate;
6). 2', 5'-dideoxyadenosine-3'-($\beta\gamma$-imino-triphosphate);
7). 2', 5'-dideoxyadenosine-3'-($\beta\gamma$-methylene-triphosphate);
8). 2', 5'-dideoxyadenosine-3'-O-thiophosphate;
9). 2', 5'-dideoxyadenosine-3'-(2-O-thiodiphosphate);
10). 2', 5'-dideoxyadenosine-3'-(3-O-thiotriphosphate);
11). 2'-deoxyadenosine-3'-diphosphate;
12). 2'-deoxyadenosine-3'-triphosphate;
13). 2'-deoxyadenosine-3'-tetraphosphate;
14). 2'-deoxyadenosine-3$^1$ -($\beta\gamma$-imino-triphosphate);
15). 2'-deoxyadenosine-3'-($\beta\gamma$-methylene-triphosphate);
16). 2'-deoxyadenosine-3'-O-thiophosphate;
17). 2'-deoxyadenosine-3'-(2-O-thiodiphosphate);
18). 2'-deoxyadenosine-3'-(3-O-thiotriphosphate);
19). 9-(cyclopentyl) -2-fluoro-9H-adenine;
20). 9-(4-benzoylbenzyl)-9H-adenine;
21). 9-[(4-bis-phenyl)buten-4-yl]-9H-adenine;
22). 9-(3-monophosphoryl-cyclopentyl) -adenine;
23). 9-(3-diphosphoryl-cyclopentyl)-adenine;
24). 9-(3-triphosphoryl-cyclopentyl) -adenine;
25). 9-[3-(2-O-thiodiphosphoryl) -cyclopentyl] -adenine;
26). 9-[3-(3-O-thiotriphosphoryl) -cyclopentyl] -adenine;
27). 9-(tetrahydro-3-monophosphoryl-2-furyl) -adenine;
28). 9-(tetrahydro-3-diphosphoryl-2-furyl) -adenine;
29). 9-(tetrahydro-3-triphosphoryl-2-furyl) -adenine;
30). 9-[tetrahydro-3-(2-O-thiodiphosphoryl) -2-furyl] -adenine;
31). 9-[tetrahydro-3-(3-O-thiotriphosphoryl) -2-furyl]-adenine; and
32). P$^1$-2', 5'-dideoxyadenosine-3'-P$^3$-4-(2-aminoethyl)-aniline triphosphate.

Furthermore, the present invention discloses a method for the inhibition of adenylyl cyclase activity. The method involves the addition of an adenine-or 3'-adenosine derivative to a cell extract containing adenylyl cyclase and expressing adenylyl cyclase activity, allowing the adenine and 3'-adenosine-derivatives to react with the adenylyl cyclase and determining the amount of inhibition of adenylyl cyclase activity. The adenine-and 3'-adenosine derivatives are selected from the following:

1). 2', 5'-dideoxyadenosine-3'-[2-([(5-dimethylamino-1-naphthalenesulfonamido) (N-methyl)]-aminoethyl) -phosphate];
2). 2', 5'dideoxyadenosine-3'-[(3-cholesteryl)-phosphate];
3). 2', 5'-dideoxyadenosine-3'-diphosphate;
4). 2', 5'-dideoxyadenosine-3'-triphosphate;
5). 2', 5'-dideoxyadenosine-3'-tetraphosphate;
6). 2', 5'-dideoxyadenosine-3'-($\beta\gamma$T-imino-triphosphate);
7). 2', 5'-dideoxyadenosine-3'-($\beta\gamma$-methylene-triphosphate);
8). 2', 5'-dideoxyadenosine-3'-O-thiophosphate;
9). 2', 5'-dideoxyadenosine-3'-(2-O-thiodiphosphate);
10). 2', 5'-dideoxyadenosine-3'-(3-O-thiotriphosphate);
11). 2'-deoxyadenosine-3'-diphosphate;
12). 2'-deoxyadenosine-3'-triphosphate;
13). 2'-deoxyadenosine-3'-tetraphosphate;
14). 2'-deoxyadenosine-3'-($\beta\gamma$-imino-triphosphate);
15). 2'-deoxyadenosine-3'-($\beta\gamma$-methylene-triphosphate);
16). 2'-deoxyadenosine-3'-O-thiophosphate;
17). 2'-deoxyadenosine-3'-(2-O-thiodiphosphate);
18). 2'-deoxyadenosine-3'-(3-O-thiotriphosphate);
19). 9-(cyclopentyl)-2-fluoro-9H-adenine
20). 9-(4-benzoylbenzyl)-9H-adenine
21). 9-[(4-bis-phenyl)buten-4-yl]-9H-adenine
22). 9-(3-monophosphoryl-cyclopentyl)-adenine
23). 9-(3-diphosphoryl-cyclopentyl)-adenine
24). 9-(3-triphosphoryl-cyclopentyl)-adenine;
25). 9-[3-(2-O-thiodiphosphoryl) -cyclopentyl] -adenine;
26). 9-[3-(3-O-thiotriphosphoryl) -cyclopentyl] -adenine;
27). 9-(tetrahydro-3-monophosphoryl-2-furyl) -adenine;
28). 9-(tetrahydro-3-diphosphoryl-2-furyl) -adenine;
29). 9-(tetrahydro-3-triphosphoryl-2-furyl) -adenine;
30). 9-[tetrahydro-3-(2-O-thiodiphosphoryl) -2-furyl] -adenine;
31). 9-[tetrahydro-3-(3-O-thiotriphosphoryl) -2-furyl]-adenine;
34). adenosine-3'-diphosphate; and
35). adenosine-3'-triphosphate.

DETAILED DESCRIPTION OF THE INVENTION

The 3'-adenosine derivatives of the present invention were prepared according to the following methods.

Synthesis of Compounds

Syntheses of 2', 5'-dideoxyadenosine-3'-[2-([(5-dimethylamino-1-naphthalenesulfonamido) -(N-methyl)] -aminoethyl) -phosphate] (1) and 2', 5'-dideoxyadenosine-3'-[(3-cholesteryl)-phosphate] (2) proceeded as per Schemes 1 and 2, respectively. These syntheses are according to the methods described by Desaubry et al.[40] Syntheses of the nucleotides 3, 4, 5, 6, 7, 11, 12, 13, 14, and 15 are performed as per Scheme 3, according to the methods described by Désaubry et al.[41,42]. Synthesis of 2', 5'-dideoxyadenosine-3'-O-thiophosphate (8) is performed according to Scheme 4. Scheme 5 depicts the syntheses of the 3'-O-thiodiphosphate derivatives of 2', 5'-dideoxyadenosine (9), 2'-deoxyadenosine (17), 9-(cyclopentyl)-adenine (25), and 9-(tetrahydro-2-furyl)-adenine (30), by variants of the methods of Désaubry et al. [41,42]. The syntheses of the corresponding 3'-O-thiotriphosphate derivatives (10, 18, 26, and 31) are performed according to scheme 6, by variants of the methods of Désaubry et al. [41,42]. Synthesis of the 2'-deoxyadenosine-3-O-thiophosphate (16) was as per Scheme 7, according to methods described herein. Synthesis of nucleoside 19 is performed as per Scheme 8, according to methods described herein. Synthesis of nucleoside 20 followed Scheme 9, according to methods described herein. Synthesis of nucleoside 21 followed Scheme 10, according to methods described herein. Syntheses of nucleotides 22, 23, and 24 follow Scheme 11 and syntheses of nucleotides 27, 28, and 29 follow Scheme 12. Synthesis of the nucleotide-linker conjugate 32 follows Scheme 13, according to methods described by Désaubry and Johnson[43].

Scheme 1

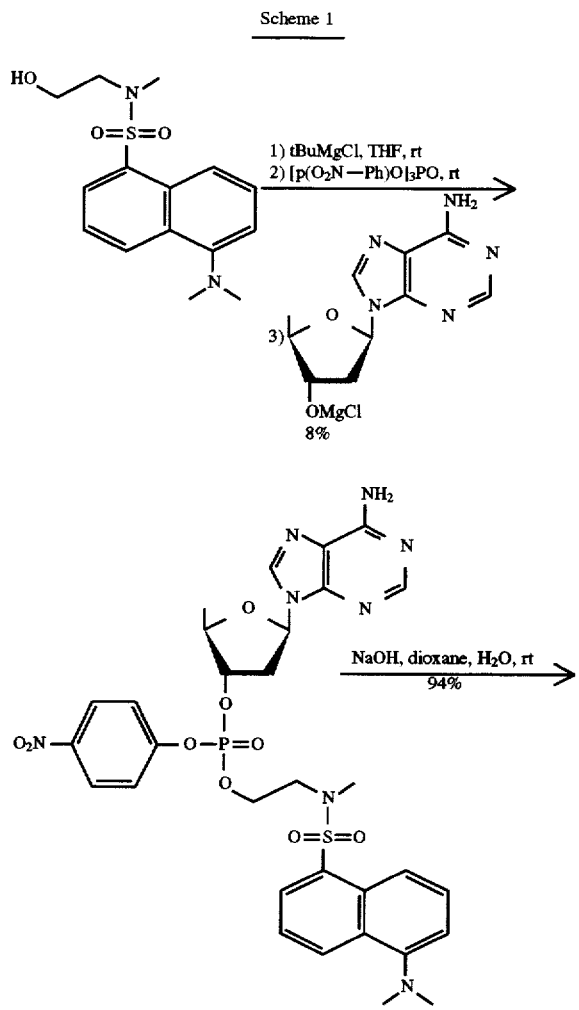

-continued
Scheme 1

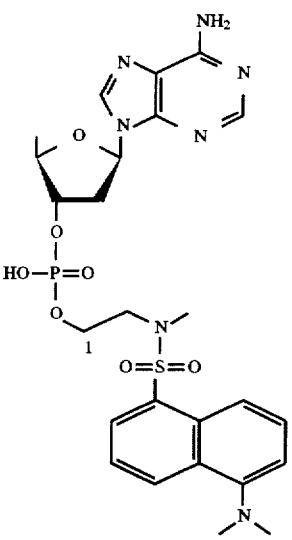

Synthesis of 4-nitrophenyl-|N-(5-dimethylamino-1-naphthalenesulfonamido) -N-methyl| -2-aminoethyl-2', 5'-dideoxyadenosine-3'-phosphate 4-Nitrophenyl |N-(5-dimethylamino-1-naphthalenesulfonamido) -N-methyl| -2-aminoethyl-2', 5'-dideoxyadenosine-3'-phosphate was prepared as follows[40]. To a solution of the dansyl derivative, N-(5-dimethylamino-1-naphthalenesulfonamido) -N-methyl-2-ethanolamine[40] (0.93 g, 3 mmol) in THF (30 ml) at 15° C. was added dropwise a 1.0M solution of tert-butyl magnesium chloride (3 ml, 3 mmol) in THF. After stirring for 5 min, tris-(p-nitrophenyl) phosphate (1.38 g, 3 mmol) was added and stirring was continued for 90 min under argon. The resulting solution was subjected directly to the next step (one-pot linkage of the nucleoside) without further treatment. A 1.0M solution of tert-butyl magnesium chloride (3 ml, 3 mmol) in THF was added dropwise to a suspension of 2', 5'-dideoxyadenosine (0.71 g, 3 mmol) in THF ($_{50}$ ml). After stirring 5 min, the solution of the phosphorylated adduct, prepared as above, was added dropwise to this mixture in 30 min. The mixture was stirred at room temperature for 4 h. It was then concentrated in vacua, $_{50}$ ml of water was added, and this solution was extracted 3 times with 30 ml of EtOAc. The combined organic layers were washed with brine, dried over MgSO$_4$, and concentrated in vacuo to give a gum which was subjected to flash chromatography (EtOAc/EtOH, 90/10), affording 4-nitrophenyl-[N-(5-dimethylamino-1-naphthalene sulfonamido)-N-methyl]-2-aminoethyl-2', 5'-dideoxy adenosine 3'-phosphate (0.18 g, 8%).

$^1$H NMR (CDCl$_3$) δ 1.43 (d, 3H, H-5'); 2.65–2.85 (m, 1H, H-2'α); 2.85 (s, 6H, N(CH$_3$)$_2$) ; 2.86 (s, 3H, SO$_2$N(CH$_3$)), 3.1–3.3 (m, 1H, H-2'β); 3.59 (t, 2H, N—CH$_2$); 4.25–4.5 (m, 3H, CH$_2$—O—P and H-4') ; 5.17 (m, 1H, H-3') ; 6.33 (m, 1H, H-1'); 7.16 (d, 1H, H-dansyl); 7.25 (s, 2H, NH$_2$) 7.41 (d, 2H, H—Ph—NO$_2$); 7.48–7.56 (m, 2H, H-dansyl); 7.96 (s, 1H, H-2); 8.12 (m, 1H, H-dansyl); 8.15–8.31 (m, 4H, H-dansyl, H—Ph—NO₂ and H-8).

Synthesis of 2', 5'-dideoxyadenosine-3'-|2-(|(5-dimethylamino-1-naphthalenesulfonamido)-(N-methyl)|-aminoethyl)-phosphate| (1)

2', 5'-Dideoxyadenosine-3'-|2-(|(5-dimethylamino-1-naphthalenesulfonamido) -(N-methyl)| -aminoethyl) -phosphate| (1) or triethylammonium |N-(5-dimethylamino-1-naphthalenesulfonamido) -N-methyl|-2-aminoethyl-2', 5'-dideoxyadenosine-3'-phosphate (1) was prepared according to the following procedure[40], given in Scheme 1. To a solution of the precedent phosphate triester (0.11 g, 0.15 mmol) in dioxane (4 ml) was added a 1M solution of NaOH (0.4 ml). The reaction mixture was allowed to stir overnight at room temperature. Then it was concentrated in vacuo, diluted with ₅₀ ml of water, neutralized with a 1M solution of HCl, washed twice with EtOAc (20 ml), and subjected to DEAE-Sephadex column chromatography eluting with a 0.01–1M triethylammonium bicarbonate linear gradient. The appropriate fractions were pooled and desalted by repeated evaporations of portions of MeOH under vacuum to afford 0.10 g (94%) of 1 as a green glass. ¹H NMR (CDCl₃) δ 1.17–1.39 (m, 12H, H-Et₃N and H-5'); 2.70–3.10 (m, 17H, H-2', N(CH₃)₂, SO₂N(CH₃), and H-Et₃N); 3.48 (t, 2H, N-CH₂); 4.03–4.10 (m, 2H, CH₂-O-P); 4.30 (m, 1H, H-4'); 4.69 (m, 1H, H-3'); 6.31–6.37 (m, 3H, H-1'and NH2); 7.13 (d, 1H, H-dansyl); 7.44–7.54 (q, 2H, H-dansyl); 7.97 (s, 1H, H-2); 8.09 (d, 1H, H-dansyl); 8.26 (s, 1H, H-8); 8.28 (d, 1H, H-dansyl); 8.49 (d, 1H, H-dansyl).

Synthesis of cholesteryl-4-nitrophenyl 2', 5'-dideoxyadenosine-3'-phosphate

Cholesteryl-4-nitrophenyl 2', 5'-dideoxyadenosine-3'-phosphate was prepared as follows[40], as included in Scheme 2. A 1.0M solution of tert-butyl magnesium chloride (5 ml, 5 mmol) in THF was added dropwise to a suspension of 2', 5'-dideoxyadenosine (1.18 g, 5 mmol) in THF (₅₀ ml). After stirring for 10 min, tris-(p-nitrophenyl) phosphate (2.31 g, 5 mmol) was added, and stirring was continued for 90 min under argon. The resulting solution was subjected directly to the next step (one-pot linkage of the nucleoside) without further treatment. To a solution of cholesterol (1.93 g, 5 mmol) in THF (20 ml) a 1.0M solution of tert-butyl magnesium chloride (5 ml, 5 mmol) in THF was added dropwise at room temperature. After stirring 15 min the solution of the phosphorylated adduct, prepared as above, was added dropwise to this mixture in 30 min. The mixture was stirred at room temperature for 3 h and then concentrated in vacuo, diluted with 150 ml of EtOAc, and washed with a 0.5M solution of NaHCO₃ (150 ml). The organic layer was washed with brine, dried over MgSO₄, and concentrated in vacuo to give a gum which was subjected to flash chromatography (CH₂Cl₂/acetone, 95/5, followed by CH₂Cl₂/EtOH, 95/5) affording the title compound (2.23 g, 54%). ¹H NMR (CDCl₃) δ 6 0.65–3.07 (m, H-2', H-5'and H-cholesteryl); 4.22–4.37 (m, 2H, CH—O—P and H-4'); 5.08 (m, 1H, H-3'); 5.38 (s, 1H, H-6 cholesteryl); 6.17 (broad s, 2H, NH₂); 6.30 (m, 1H, H-1'); 7.39 (d, 2H, H—Ph); 7.92 (s, 1H, H-2); 8.25 (d, 2H, H—Ph); 8.31 (s, 1H, H-8)

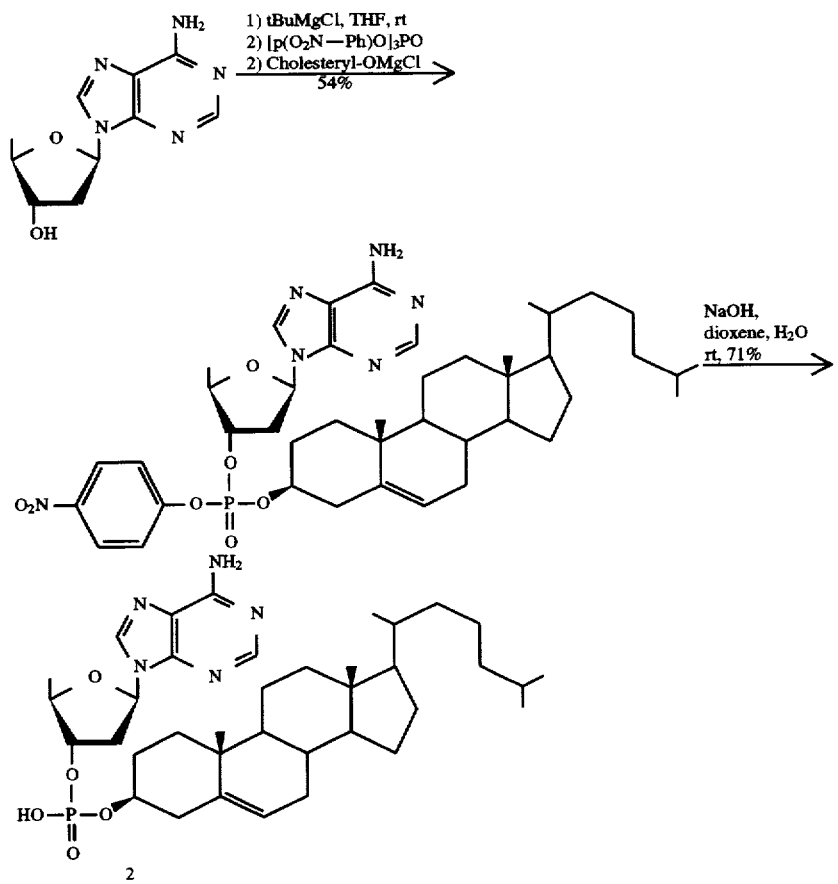

Scheme 2

Synthesis of 2', 5'dideoxyadenosine-3'-[(3-cholesteryl)-phosphate] (2)

2', 5'-Dideoxyadenosine-3'-[(3-cholesteryl) -phosphate] (2) or sodium cholesteryl 2', 5'-dideoxyadenosine-3'-phosphate (2) was prepared according to the following procedures[40]. To a solution of cholesteryl 4-nitrophenyl 2', 5'-dideoxyadenosine-3'-phosphate (0.66 g, 0.8 mmol) in methanol (25 ml) was added a 1.0M solution of NaOH (3.2 ml). The reaction mixture was allowed to stir overnight at room temperature. Then it was concentrated in vacuo. The precipitate was washed successively with a 1.0M solution of HCl, EtOH, EtOAc, 0.1 M NaOH, water and EtOH to give 2 (0.28 g, 71%). To get this salt in solution one equivalent of tetrabutylammonium fluoride was added.

$^1$H NMR (CDCl$_3$) δ 0.65–3.07 (m, H-2', H-5', nBu$_4$N and H-cholesteryl) ; 4.15–4.24 (m, 1H, H-4'); 4.25–4.33 (m, 1H, CH—O—P); 4.82–4.85 (m, 1H, H-3'); 5.37 (s, 1H, H-6 cholesteryl); 5.83 (broad s, 2H, NH$_2$); 6.30 (m, 1H, H-1'); 7.91 (s, 1H, H-2) ; 8.31 (s, 1H, H-8).

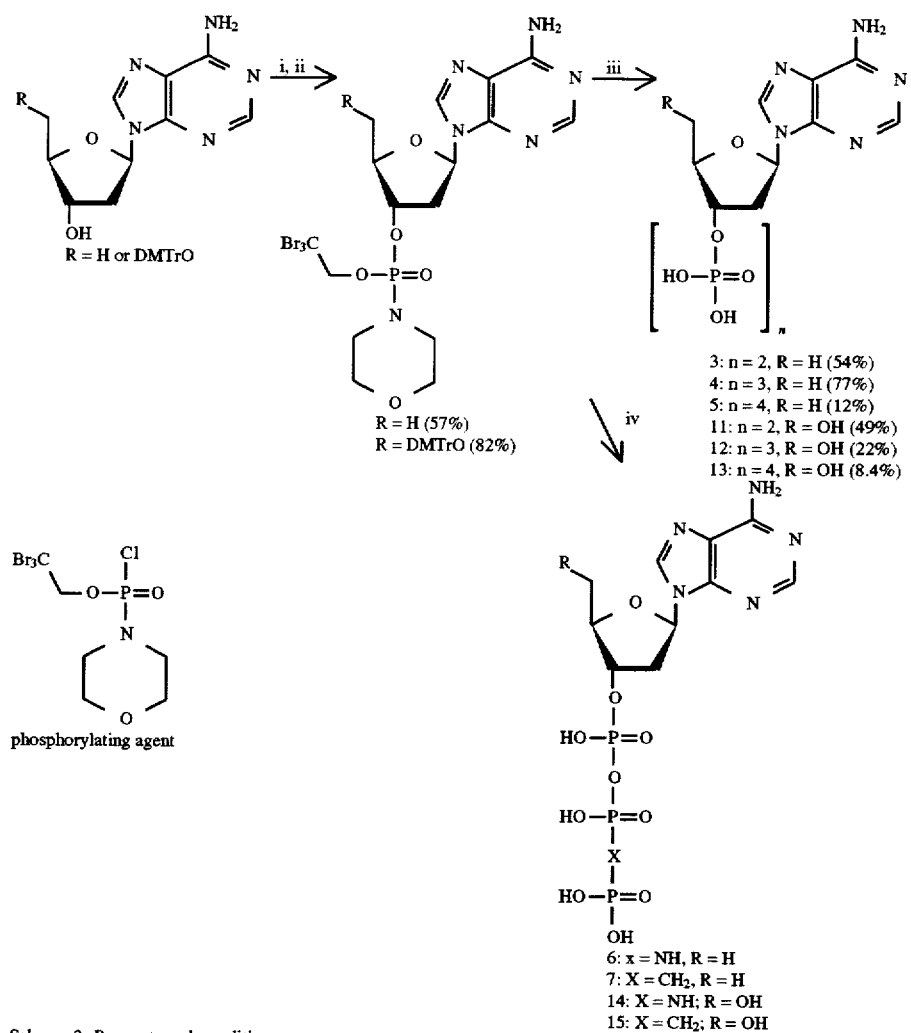

Scheme 3: Reagents and conditions:

i, tert-BuMgCl, THF, rt;

ii, phosphorylating agent, rt;

iii, Zn, (Bu$_3$N)$_3$H$_3$PO$_4$, (Bu$_3$N)$_2$H$_4$P$_2$O$_7$ or (Bu$_3$N)$_3$H$_5$P$_3$O$_{10}$, pyridine, rt, followed by AcOH 80%, rt, 30 min for 11, 12, and 13;

iv, Zn, BuN(H$_2$O$_3$P)$_2$NH or (Bu$_3$N)$_2$(H$_2$O$_3$P)$_2$CH$_2$, pyridine, rt, followed by AcOH 80%, rt, 30 min for 14 and 15.

Specific reagents and conditions for Scheme 3 are as follows: i, tert-butyl-magnesium chloride, THF, rt; ii phosphorylating agent, rt; iii, Zn, (Bu$_3$N)$_3$H$_3$PO$_4$, (Bu$_3$N)$_2$H$_4$P$_2$O$_7$ or (Bu$_3$N)$_3$H$_5$P$_3$O$_{10}$, pyridine, rt, followed by AcOH 80%, rt, 30 min for 11, 12 and 13; iv, Zn, BU$_3$N (H$_2$O$_3$P)$_2$NH or (Bu$_3$N)$_2$(H$_2$O$_3$P)$_2$CH$_2$, pyridine, rt, followed by ACOH 80%, rt, 30 min for 14 and 15.

Synthesis of 2', 5'-dideoxyadenosine-3'-0-[(2,2,2-tribromoethyl)-morpholinophosphonate]

2', 5'-Dideoxyadenosine-3'-O-[(2,2,2-tribromoethyl)-morpholinophosphonate][42] was prepared as follows, as included in Scheme 3.

To a suspension of 2', 5'-dideoxyadenosine (1.18 g, 5 mmol) in a mixture of THF (60 ml) and pyridine (10 ml) was added dropwise at room temperature a 0.9M solution of tert-butyl-magnesium chloride (5.55 ml, 5 mmol) in THF. After stirring for 5 min., 2,2,2-tribromoethyl phosphoro-morpholino-chloridate (2.25 g, 5 mmol) was added, and stirring was continued for 1.5 h. The mixture was then concentrated in vacuo, diluted with EtOAc (30 ml), quenched with water (60 ml) and then extracted with EtOAc (30 ml×2). The combined organic layers were washed with a saturated solution of NaCl, were dried over $Na_2SO_4$, and then were evaporated to give a gum. The crude product was subjected to silica gel chromatography. Elution with $CH_2Cl_2$:$Et_2O$ (95:5) followed by $Ch_2Cl_2$:MeOH (95:5) afforded a mixture of the two diastereo-isomers of the adduct (1.61 g, 57%): $R_f$ 0.45 and 0.34 ($CH_2Cl_2$-MeOH, 95:5); $^1H$ NMR ($CDCl_3$, the more polar diastereoisomer) δ 1.23 (d, 3H, J=6.9 Hz, H-5'), 2.71–2.80 (m, 1H, H-2"), 2.99–3.10 (m, 1H, H-2'), 3.26 (m, 4H, morpholine), 3.69 (m, 4H; morpholine), 4.40 (m, 1H, H-4'), 4.59–4.76 (m, 2H, $CH_2CBr_3$), 5.01 (m, 1H, H-3'), 6.02 (s, 2H, $NH_2$), 6.35 (t, 1H, J=6.7 Hz, H-1'), 7.92 (s, 1H, H-2), 8.31 (s, 1H, H-8); $^1H$ NMR ($CDCl_3$, the less polar diastereoisomer) δ 1.40 (d, 3H, J=6.6 Hz, H-5'), 2.71–2.81 (m, 1H, H-2"), 2.97–3.08 (m, 1H, H-2'), 3.06 (m, 4H, morpholine), 3.64 (m, 4H, morpholine), 4.32 (m, 1H, H-4'), 4.55–4.73 (m, 2H, $CH_2CBr_3$), 4.97 (m, 1H, H-3'), 6.30 (t, 1H, J=6.6 Hz, H-1'), 6.41 (s, 2H, $NH_2$), 7.89 (s, 1H, H-2), 8.25 (s, 1H, H-8).

Synthesis of 5'-O-(dimethoxytrityl)-2'-deoxyadenosine-3'-O-[(2,2,2-tribromoethyl)-morpholino-phosphonate]

5'-O-(dimethoxytrityl)-2'-deoxyadenosine-3'-O-[(2,2,2-tribromoethyl)-morpholino-phosphonate][42] was prepared from 5'-O-(dimethoxytrityl)-2'-adenosine[44] as described above for the synthesis of the precedent compound (cf. Scheme 3), except the reaction was carried out in THF without adding pyridine, with a yield of 82%: $R_f$ 0.50 and 0.46 ($CH_2Cl_2$-MeOH, 95:5). $^1H$ NMR ($CDCl_3$, mixture of the two diastereoisomers) δ 2.81-2.87 (m, 1H, H-2"), 3.01–3.04 (m, 1H, H-2'), 3.16–3.26 (m, 4H, morpholine), 3.37–3.51 (m, 1H, H-5'), 3.64–3.72 (m, 4H, morpholine), 3.75 (s, 6H, $OCH_3$), 4.43 (m, 1H, H-4'), 4.52–4.74 (m, 2H, $CH_2CBr_3$), 5.28 (m, 1H, H-3'), 6.24 (br s, 2H, $NH_2$), 6.44–6.52 (m, 4H, H-aryl), 7.20–7.27 (m, 9H, H-aryl), 7.94 and 7.96 (s, 1H, H-2), 8.24 and 8.26 (s, 1H, H-8).

Synthesis of 2', 5'-dideoxyadenosine-3'-diphosphate (3)

2', 5'-Dideoxyadenosine-3'-diphosphate (3) was prepared according to the following procedure[41] (Scheme 3). 2', 5'-dideoxy-adenosine-3-0-[(2,2,2-tribromoethyl)-morpholinophosphonate][42] (1.42 g, 2.5 mmol) reacted with mono (tri-n-butylammonium) -phosphate (30 mmol), as described above, yielding 1.35 mmol (54%) of 2', 5'-dideoxyadenosine-3'-diphosphate (3). $^1H$ NMR ($D_2O$) δ 1.30 (d, 3H, J=6.6 Hz, 3H-5'), 2.79–2.87 (m, 2H, H-2' and H-2"), 4.36–4.39 (m, 1H, H-4'), 4.72–4.79 (m, 1H, H-3'), 6.33 (t, 1H, J=6.6 Hz, H-1'), 8.06 (s, 1H, H-2), 8.25 (s, 1H, H-8); $^{31}P$ NMR ($D_2O$) δ −7.05 (dd, $J_{P-H}$=7.6 Hz, $J_{P-P}$=21.1 (Hz, P-1), −1.77 (d, J=21.1 Hz, P-2) ; FAB-MS 394 (M—H)+.

Synthesis of 2', 5'-dideoxyadenosine-3'-triphosphate (4)

2', 5'-Dideoxyadenosine-3'-triphosphate (4) was prepared according to the following procedure[41]. 2', 5'-dideoxyadenosine 3'-O-[(2,2,2-tribromoethyl) morpholinophosphonate][42] (0.89 g, 1.5 mmol) was added to a solution of pyridine (30 ml) containing activated zinc[45] (0.15 g) and bis(tri-n-butylammonium)-pyrophosphate (15 mmol), under the exclusion of moisture. The mixture was stirred at room temperature during two days. Then, the reaction mixture was centrifuged, and the supernatant was evaporated in vacuo and purified by QAE-Sephadex ($HCO^3$-form) with a linear gradient of triethylammonium bicarbonate (0.01–0.4M). The appropriate fractions were lyophilized and then co-evaporated several times with methanol, yielding 1.16 mmol (77%) of 2', 5'-dideoxyadenosine-3'-triphosphate (4).

The nucleotide 4 was isolated as its sodium salt by addition of 1M sodium iodide in acetone to a methanol solution of the triethylammonium nucleotide. The precipitate was centrifuged and washed three times with cold acetone and dried in vacuo giving the sodium salt of 2', 5'-dideoxy-3'-adenosine triphosphate. No impurities were noted on ion exchange HPLC.

$^1H$ NMR ($D_2O$) δ 2.44 (d, 3H, J=7.1 Hz, 3H-5'), 2.7–2.8 (m, 1H, H-2'), 2.85–3.0 (m, 1H, H-2'), 4.39 (m, 1H, H-4'), 6.42 (t, 1H, J=6.9 Hz, H-1), 8.19 (s, 1H, H-2), 8.33 (s, 1H, H-8); $^{31}P$ NMR ($D_2O$) δ −15.55 (dd, J=19.1 Hz, P-2), −7.55 (dd, $J_{P-H}$=7.5 Hz, $J_{P-P}$=17.9 Hz), 1.08 (d, J=18.4 Hz); FAB-MS 496 (M-2H +NA)+.

Synthesis of 2', 5'-dideoxyadenosine-3'-tetraphosphate (5)

2', 5'-Dideoxyadenosine-3'-tetraphosphate (5) was prepared according to the following procedures (Scheme 3). 2', 5'-Dideoxyadenosine 3'-O-[(2,2,2-tribromoethyl)-morpholinophosphonate][42] (0.89 g, 1.5 mmol) was added to a solution of pyridine (80 ml) containing activated zinc[45] (0.15 g) and tributylammonium salt of triphosphoric acid (15 mmol, 15 mmol), under the exclusion of moisture. The mixture was stirred at room temperature during two days. Then, the reaction concentrated in vacuo, diluted with cold water (300 ml), filtered and purified by QAE-Sephadex ($HCO_3$-form) with a linear gradient of triethylammonium bicarbonate (0.1–1M). The appropriate fractions were lyophilized and then co-evaporated several times with methanol, yielding 0.18 mmol of 2', 5'-dideoxy-3'-adenosine tetraphosphate (5). This nucleotide was isolated as its sodium salt by addition of 1M sodium iodide in acetone to a methanol solution of the triethylammonium nucleotide. The precipitate was centrifuged and washed three times with cold acetone and dried in vacuo giving the sodium salt of 2', 5'-dideoxy-3'-adenosine tetraphosphate (5). $^1H$ NMR ($D_2O$) δ 1.41 (d, 3H, J=6.5 Hz, 3H-5'), 2.80–3.00 (m, 2H, H-2'and H-2"), 6.52 (t, 1H, J=6.9 Hz, H-1'), 8.28 (s, 1H, H-2), 8.47 (s, 1H, H-8); $^{31}P$ NMR ($D_2O$) δ −18.55 (t, J 17.1 Hz, P-3), −17.80 (t, J=19.2 Hz, P-2), −8.09 (dd, $J_{P-H}$=9.1 Hz, $J_{P-P}$= 18.1 Hz, P-1), −1.55 (d, J=13.8 Hz, P-4).

Synthesis of 2', 5'-dideoxyadenosine-3'-(βγ-iminotriphosphate) (6)

2'5'-Dideoxyadenosine-3'-(βγ-imino-triphosphate) (6) is prepared according to the procedure shown in Scheme 3. The reagents and conditions are as used in the synthesis of 2', 5'-dideoxyadenosine-3'-triphosphate, except that pyrophosphoric acid is replaced with the tributylammonium salt of imidodiphosphate.

Synthesis of 2', 5'-dideoxyadenosine-3'-(βγ-methylenetriphosphate) (7)

2', 5'-Dideoxyadenosine-3'-(βγ-methylene-triphosphate) (7) is prepared according to the procedure shown in Scheme 3. The reagents and conditions are as used in the synthesis of 2', 5'-dideoxyadenosine-3'-triphosphate, except that pyrophosphoric acid is replaced with the tributylammonium salt of methylenediphosphonate.

SCHEME 4

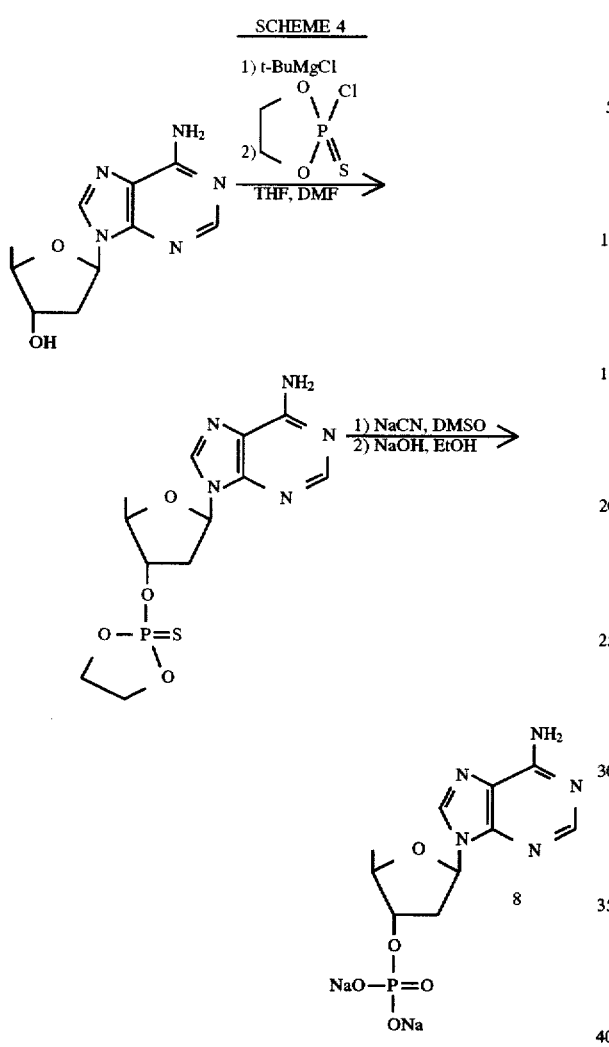

Synthesis of 2', 5'-dideoxyadenosine-3'-O-thiophosphate (8)

The synthesis of 2', 5'-dideoxyadenosine-3'-0-thiophosphate (8) was accomplished by the following procedure (Scheme 4). 2', 5'-Dideoxyadenosine (0.70 g, 3 mmol) was co-evaporated three times with dry pyridine and once with benzene. The dried nucleoside was suspended in the mixture of dry THF (40 ml) and DMF (4 ml), and 3.6 ml of tert-butylmagnesium chloride (3 mmol) was added dropwise to the above solution under the exclusion of air. After stirring the reaction mixture for 5 min, 0.83 g of 2-chloro-2-thio-1,3,2-dioxaphospholane solution in benzene (1.4:1 v/v), prepared as per Yamasaki and Sato[46], was added and stirring was continued for a further 1.5 h. Then the solvent was removed in vacuo and the residue was taken in water, neutralized with a solution of $NaHCO_3$ and extracted with EtOAc (3×25 ml). The solvent from the pooled organic phases was evaporated in vacuo giving 1.0 g of yellowish oil. The product was immediately dissolved in 30 ml of a solution of NaCN (0.59 g; 12 mmol) and stirred overnight under reduced pressure at rt. After 16 hours, 20 ml of NaOH in EtOH (0.18 g ; 4.5 mmol) was added and stirring was maintained for 2 hours followed by partial removal of the solvent in vacuo. Then the mixture was washed with AcOEt and diluted with water to 600 ml. The compound was purified by ion-exchange chromatography and eluted with a linear gradient (0.1–0.4M) of triethylammonium bicarbonate, affording 0.60 g (1.82 mmol, 61% yield) of 2', 5'-dideoxyadenosine-3'-O-thiophosphate (8), showing a single peak on HPLC. $^1$H NMR (250 MHz, $D_2O$ ) δ 1.37 (d, 3H, J=6.6 Hz, H-5'); 2.79 (m, 1H, H-2') ; 2.89 (m, 1H, H-21") ; 4.38 (m, 1H, H-4'); 4.40 (m, 1H, H-3'); 6.40 (t, 1H, J=6.9 Hz, H-1'); 8.18 (s, 1H, H-2), 8.36 (s, 1H, H-8). $^{31}$P NMR (101 MHz, $D_2O$ ) δ 47.26 (d, J=9.9 Hz)

SCHEME 5

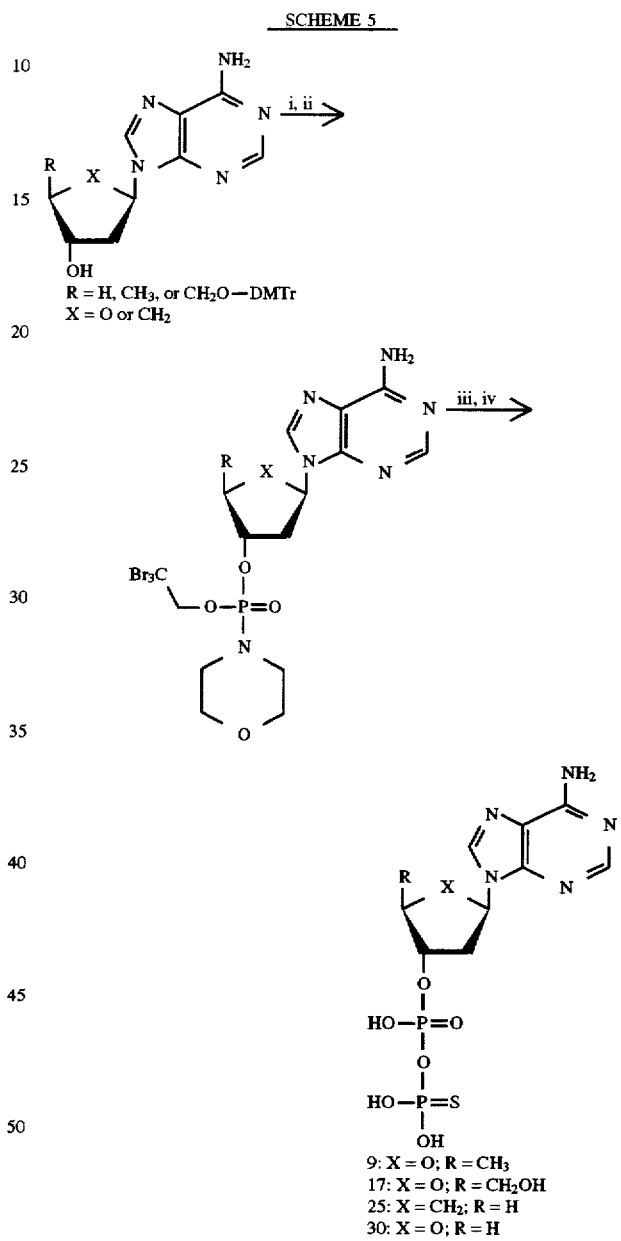

R = H, $CH_3$, or $CH_2O$—DMTr
X = O or $CH_2$

9: X = O; R = $CH_3$
17: X = O; R = $CH_2OH$
25: X = $CH_2$; R = H
30: X = O; R = H

Scheme 5: Reagents and conditions:

i) tert-BuMgCl, THF, rt;

ii) phosphorylating agent, rt;

iii) Zn, NC—$CH_2$—$CH_2$—S—$PO_3HBu_3N$,
pyridine, rt, followed by AcOH 80%, rt, 30 min for deprotection of the 5'-hydroxy when required (R = OH);

iv) $Et_3N$.

Specific reagents and conditions for Scheme 5 are as follows: i. tert-BuMgCl, THF, rt; ii. phosphorylating agent, rt; iii. NC—$CH_2$—$CH_2$—S—$PO_3H$ $Bu_3N$, pyridine, rt, followed by AcOH 80%, rt, 30 min for deprotection of the 5'-hydroxy when required (R=OH); iv. Et₃N.

Synthesis of 2', 5'-dideoxyadenosine-3'-(2-O-thiodiphosphate) (9)

The synthesis of 2', 5'-dideoxyadenosine-3'-(2-O-thiodiphosphate) (9) proceeds as shown in Scheme 5, with reagents and conditions given. This procedure is based on the previously described procedure for the synthesis of 2', 5'-dideoxyadenosine-3'-diphosphate (3) (Scheme 3). The reagent NC—CH₂—CH₂—S —PO₃H given here was prepared according to Burgers and Eckstein[47] and is used instead of the phosphoric acid that was used in the preparation of compound (3).

SCHEME 6

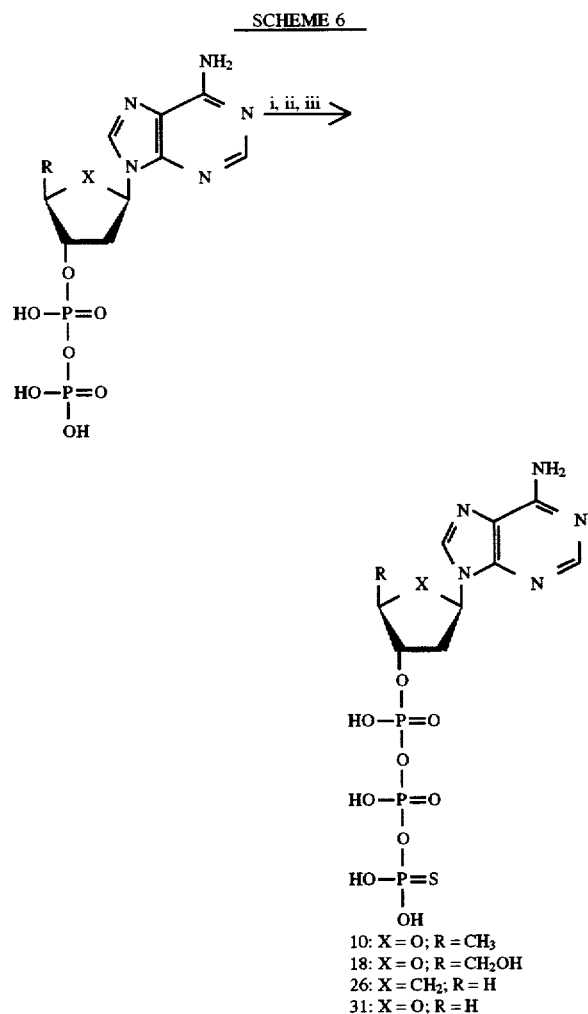

10: X = O; R = CH₃
18: X = O; R = CH₂OH
26: X = CH₂; R = H
31: X = O; R = H

Scheme 6: Reagents and conditions:

i) (PhO)₂POCl;

ii) NC—CH₂—CH₂—S—PO₃H;

iii) Et₃N.

Specific reagents and conditions for Scheme 6 are as follows: i. (PhO)₂POCL; ii. NC—CH₂—CH₂—S —PO₃H; iii. Et₃N.

Synthesis of 2', 5'-dideoxyadenosine-3'-(3-O-thiotriphosphate) (10)

The synthesis of 2', 5, -dideoxyadenosine-3'-(3-O-thiotriphosphate) (10) proceeds from 2', 5'-dideoxyadenosine-3'-diphosphate (3) as shown in Scheme 6, with reagents and conditions given. This procedure is based on earlier work of Eckstein and colleagues.[48,49] The reagent NC—CH₂—CH₂—S —PO₃H was prepared according to Burgers and Eckstein[47].

Synthesis of 2'-deoxyadenosine-3'-diphosphate (11)

2'-deoxyadenosine-3'-diphosphate (11) was prepared according to the following procedures (Scheme 3)[42]. 5'-0-(dimethoxytrityl)-2'-deoxyadenosine-3'-0-|(2,2,2-tribromoethyl)-morpholinophosphonate|[42] (0.55 g, 1 mmol) reacted with mono (tri-n-butylammonium) -phosphate (30 mmol), as described above, yielding 0.49 mmol (49%) of 2'-deoxyadenosine-3'-diphosphate (11). ¹H NMR (D₂O) δ 2.57–2.62 (m, 2H, H-2' and H-2"), 3.49 (d, 2H, J=4.75, Hz, 2H-5'), 4.07–4.11 (m, 1H, H-4'), 6.22 (t, 1H, J=7.0 Hz, H-1'), 7.96 (s, 1H, H-2), 8.10 (s, 1H, H-8). ³¹P NMR (D₂O) δ −6.75 (dd, JP-H=7.4 Hz, $J_{P—P}$=20.3 Hz, P-1), −1.35 (d, J=20.3 Hz, P-2). FAB-MS 410 (M—H)+.

Synthesis of 2'-deoxyadenosine-3'-triphosphate (12)

2'-Deoxyadenosine-3'-triphosphate (12) was prepared according to the following procedures (Scheme 3)[42]. 5'0-(dimethoxytrityl)-2'-deoxyadenosine-3'-0-|(2,2,2-tribromoethyl)-morpholinophosphonate|[42] (2.37 g, 2.5 mmol) was added to a solution of pyridine (30 ml) containing activated zinc (0.25 g) and bis(tri-n-butylammonium)-pyrophosphate (25 mmol), under the exclusion of moisture. The mixture was stirred at room temperature during two days. Then, the reaction mixture was centrifuged, and the supernatant was evaporated in vacuo and treated with 80% acetic acid at room temperature for 30 min. The medium was then neutralized with a cold solution of 0.5M NaHCO₃, diluted to two liters, filtered, and then purified by chromatography on QAE-Sephadex as above, yielding 0.55 mmol (22%) of 2'-deoxy-3'-adenosine triphosphate (12). This nucleotide was also isolated as its sodium salt as above. No impurities were noted on ion exchange HPLC. ¹H NMR (D₂O), β2.7–2.9 (m, 2H, H₂'), 3.84 (s, 2H, 2 H-5'), 5.08 (m, 1H, H-3'), 6.47 (t, 1H, J=7 Hz, H-1'), 8.16 (s, 1H, H-2), 8.32 (s, 1H, H-8). ³¹P NMR (D₂O) δ −17.13 (dd, J=19.4 Hz, P-2); −15.66 (t, J=18.9 Hz, P-3), −7.66 (dd, $J_{P—P}$=8.0 Hz, $J_{P—P}$=18.4 Hz, P-1;). FAB-MS 490 (M—H)+.

Synthesis of 2'-deoxyadenosine-3'-tetraphosphate (13)

2'-Deoxyadenosine-3'-tetraphosphate (13) was prepared according to the following procedures (Scheme 3)[43]. 5-0-(Dimethoxytrityl) 2'-deoxyadenosine-3'-0-[(2,2,2-tribromoethyl) morpholinophosphonate][42] (1.42 g, 2.5 mmol) was added to a solution of pyridine (₅₀ ml) containing activated zinc[45] (0.5 g) and tributylammonium salt of triphosphoric acid (15 g, 15 mmol), under the exclusion of moisture. The mixture was stirred at room temperature during two days. Then, the reaction mixture was concentrated in vacuo and treated with 80% acetic acid at room temperature for 30 min. The medium was then neutralized with a cold solution of 0.5M NaHCO₃, diluted to two liters, filtered, and then purified by chromatography on QAE-Sephadex as above, yielding 0.21 mmol of 2'-deoxyadenosine-3'-tetraphosphate (13). This nucleotide was also isolated as its sodium salt as above. No impurities were noted on ion exchange HPLC. ¹H NMR (D₂O) δ 2.81–2.99 (m, 2H, H-2' H-2"), 3.88 (d, 2H, 2H-5'), 4.40–4.45 (m, 1H, H-4'), 5.06–5.19 (m, 1H, H-3'), 6.55 (t, 1H, J=6.7 Hz, H-1'), 8.26 (s, 1H, H-2), 8.40 (s, 1H, H-8) ³¹P NMR (D$_2$O) δ −18.28 (t, J=17.1 Hz, P-3), -17.24 (t, J=17.9 Hz, P-2),-8.07 (dd, J$_{P-H}$=7.7 Hz, J$_{P-P}$=19.2 Hz, P-1), −1.44 (d, J=18.4 Hz, P-4).

Synthesis of 2'-deoxyadenosine-31 -(βγ-imino-triphosphate) (14)

2'1-Deoxyadenosine-3'-(βγ-imino-triphosphate) (14) is prepared according to the procedure shown in Scheme 3. The reagents and conditions are as used in the synthesis of 2'-deoxyadenosine-3'-triphosphate (12), except that pyrophosphoric acid is replaced with the tributylammonium salt of imidodiphospahte.

Synthesis of 2'-deoxyadenosine-3'-(βγ-methylene-triphosphate) (15)

2'-Deoxyadenosine-3'-(βγ-methylene-triphosphate) (15) is prepared according to the procedure shown in Scheme 3. The reagents and conditions are as used in the synthesis of 2'-deoxyadenosine-3'-triphosphate (12), except that pyrophosphoric acid is replaced with the tributylammonium salt of methylenediphosphonate.

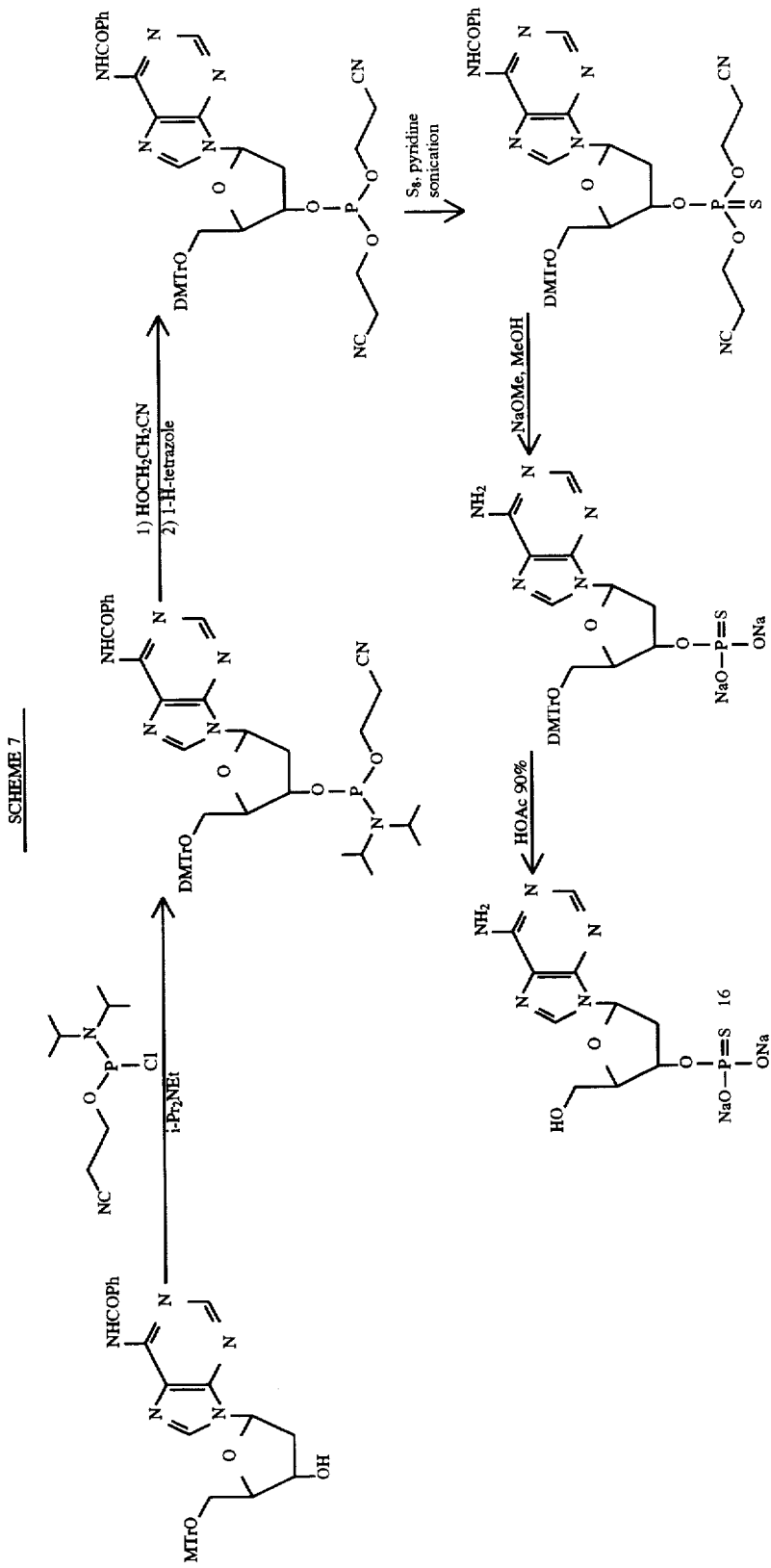
SCHEME 7

21

Synthesis of the precursor 5'-O-Dimethoxytrityl-N-6-benzoyl-2'-deoxyadenosine-3'-O-phosphorothioate triester The synthesis of the precursor 5'-O-Dimethoxytrityl-N-6-benzoyl-2'-deoxyadenosine-3'-O-phosphorothioate triester was prepared according to the following procedure (Scheme 7). 5'-O-dimethoxytrityl-N-6-benzoyl-2'-deoxyadenosine (1 g, 1.52 mmol) was dried by co-evaporation with pyridine (three times) and once with benzene, and then dissolved in dry THF (7 ml). To this solution, stirred under argon at 0°, N,N-diisopropylethylamine (1.0 ml ; 6.08 mmol) was added under anhydrous conditions, followed by 2-cyanoethyl-N,N-diisopropylchloro phosphoramidite (0.68 ml ; 3.04 mmol). After stirring for 35 min at rt, 3-hydroxypropionitrile (0.47 ml; 6.84 mmol) was added and the mixture was stirred for a further 30 min at rt. The mixture was then treated with a solution of 1-H-tetrazole (0.7 g ;10 mmol) in anhydrous acetonitrile and stirred for 16 h at rt. The solvent was then evaporated in vacuo, and the residue was partitioned between EtOAc and water. The organic phase was washed with concentrated solution of NaHCO₃, water and brine, dried over MgSO₄, and then it was concentrated in vacuo. The residual oil was dissolved in 40 ml of pyridine and sulfur (0.73 g ; 22.8 mmol) was added[50]. The mixture was sonicated at rt for 40 min and the solvent was removed in vacuo. The residue was extracted with EtOAc ($_{50}$ ml) and the unreacted sulfur was removed by filtration on celite. Then EtOAc was evaporated and the reaction mixture was purified on flash chromatography eluting with $CH_2Cl_2$:MeOH (95:5) as an eluent affording 0.93 g (1.09 mmol, 72%) of the desired triester in the form of a gum. ¹H NMR (250 MHz, CDCl₃) δ 2.6 (m, 1H, H-2'); 2.75 (m, 4H, $CH_2CN$); 3.2 (m, 1H, H-2"); 3.45 (m, 1H, H-4'); 3.8 (s, 6H, 2×$CH_3O$–); 3.8 (q, 2H, J=16 Hz, H-5'); 4.25 (m,4H, —$OCH_2$—); 4.47 (s, 1H,NH); 5.43 (q, 1H, J=5.0 Hz, H-3'); 6.42 (g, 1H, J=5.3 Hz, H-1') 6.7–7.1 (2d, 8H, J=8.73 Hz, aromatic ); 7.1–7.7 (m, 8H, aromatic); 8.0–8.1 (d, 2H, J=7.3 Hz, aromatic) ; 8.18 (s, 1H, H-8) ; 8.74 (s, 1H, H-2). ³¹P NMR (101 MHz, CDCl₃) 867.63 (dt, J=9.34 Hz).

Synthesis of 2'-deoxyadenosine-3'-O-thiophosphate (16)

The synthesis of 2'-deoxyadenosine-3'-O-thiophosphate (16) was accomplished by the following procedure (Scheme 7). 5'-O-dimethoxytrityl-6-N-benzoyl-2'-deoxyadenosine-3'-0-phosphothioate triester (0.80 g, 0.94 mmol), synthesized as above, was dissolved in 5 ml of methanol. The solution was treated with 5 ml of 25% MeONa in MeOH and stirred overnight at rt. After removal of the solvent in vacuo the residue was treated subsequently with 90% HOAc, stirred for 45 min, neutralized and purified by ion-exchange chromatography with a 0.1–0.4M linear gradient of triethylammonium bicarbonate, affording 0.31 g (0.90 mmol; 89%) of 2'-deoxyadenosine-3'-O-thiophosphate (16). The compound showed single peak on HPLC column. ¹H NMR (250 MHz, D₂O) δ 2.67–2.79 (m, 2H, H-2' H-2"); 3.77 (m, 2H, H-5'); 4.27 (m,1H, H-4'); 4.92 (m, 1H, H-3'); 6.38 (t, 1H, J=6.8 Hz, H-1'); 8.10 (s, 1H, H-2); 8.24 (s, 1H, H-8). ³¹P NMR (101 MHz, D₂O) δ 31.78 (d, J=10.6 Hz)

Synthesis of 2'-deoxyadenosine-3'-(2-O -thiodiphosphate) (17)

The synthesis of 2'-deoxyadenosine-3'-(2-O-thiodiphosphate) (17) proceeds as shown in Scheme 5 above with the reagents and conditions given. This is based on the previously described synthesis of 2'-deoxyadenosine-3'-diphosphate (11) (Scheme 3)[42]. The reagent NC—$CH_2$—$CH_2$—S —$PO_3H$ was prepared according to Burgers and Eckstein[47] and is used instead of the phosphoric acid that was used in the preparation of compound (11).

22

Synthesis of 2'-deoxyadenosine-3'-(3-O-thiotriphosphate) (18)

The synthesis of 2'-deoxyadenosine-3'-(3-O-thiotriphosphate) (18) proceeds from 2'-deoxyadenosine-3'-diphosphate (11) as shown in Scheme 6 above, with the reagents and conditions given. This is based on the earlier work of Eckstein and colleagues[48,49]. The reagent NC—$CH_2$—$CH_2$—S—$PO_3H$ was prepared according to Burgers and Eckstein[47].

SCHEME 8

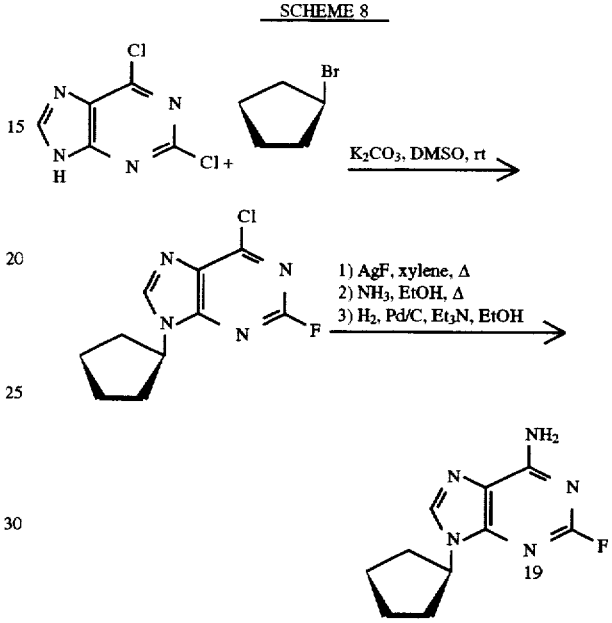

Synthesis of 9-cyclopentyl-2-fluoro-9H-adenine (19)

The synthesis of 9-cyclopentyl-2-fluoro-9H-adenine (19) was performed by the following procedure (Scheme 8). A mixture of 2,6-dichloropurine (1.46 g, 7.5 mmol), anhydrous K₂CO₃ (1.66 g, 12 mmol), cyclopentyl bromide (1.61 ml, 15 mmol) in DMSO (10 ml) was stirred at room temperature for 60 h (Scheme 8)[51]. The reaction mixture was diluted with 150 ml of water and was extracted with EtOAc (3×60 ml). The combined extracts were washed with brine, dried over MgSO₄, and concentrated in vacuo. The crude product was purified by flash chromatography on silica gel eluting with $CH_2Cl_2$-EtOH (99.7:0.3) yielding 0.59 (2.3 mmol, 31%) of 9-(cyclopentyl)-2,6-(dichloro)-9H-purine. This adduct (0.46 g, 18 mmol) was dissolved in 15 ml of dry xylene, 2.5 g of silver fluoride was added, and the mixture was refluxed and stirred under argon for 1 h. The silver salts were removed by filtration. The filtrate was returned to the reaction flask, 2.5 g of fresh silver fluoride was added, and the mixture was refluxed and stirred for 1.5 h. The silver salts were filtered off, and the filtrate was concentrated in vacuo and purified by flash chromatography on silica gel eluting with $CH_2Cl_2$-EtOH (99.7:0.3), affording 0.20 g of an inseparable mixture of monofluoro-monochloro and difluoro-compound that was dissolved in 25 ml of a concentrated solution of ammonia in MeOH. The solution was stirred at rt overnight, concentrated in vacuo, dispersed in water (25 ml), extracted with EtOAc (3×15 ml), washed with brine, dried over MgSO₄, concentrated in vacuo, and then subjected to flash chromatography on silica gel, eluting with $CH_2Cl_2$-EtOH, 98:2, giving a mixture of 2-chloro and 2-fluoro adenine derivatives. This mixture, which was not separable by chromatography, was subjected to catalytic hydrogenolysis on Pd/C during 3 days in EtOH in the presence of Et₃N (0.1 ml). The 2-chloro compound was converted into 9-cyclopentyl-9H-adenine, while the 2-fluoro compound remained unchanged. The mixture was filtered, concentrated, and then purified by flash chromatography eluting with CH$_2$Cl$_2$-MeOH, 97:3, giving 117 mg (0.53 mmol) of 9-cyclopentyl-2-fluoro-9H-adenine (19). $^1$H NMR (DMSO) δ1.65–2.14 (m, 8H, (CH$_2$)$_4$, 4.73 (t, 1H, J=14.7 Hz, H-cyclopentyl), 7.72 (br s, 2H, NH$_2$), 8.18 (s, 1H, H-8).

butanol to give 0.53 g (54%) of 9-(4-benzoylbenzyl)-9H-adenine (20). $^1$H NMR (DMSO) δ 5.49 (s, 2H, CH$_2$), 7.27–7.71 (m, 9H, H-Ar), 8.15 (s, 1H, H-2), 8.30 (s, 1H, H-8).

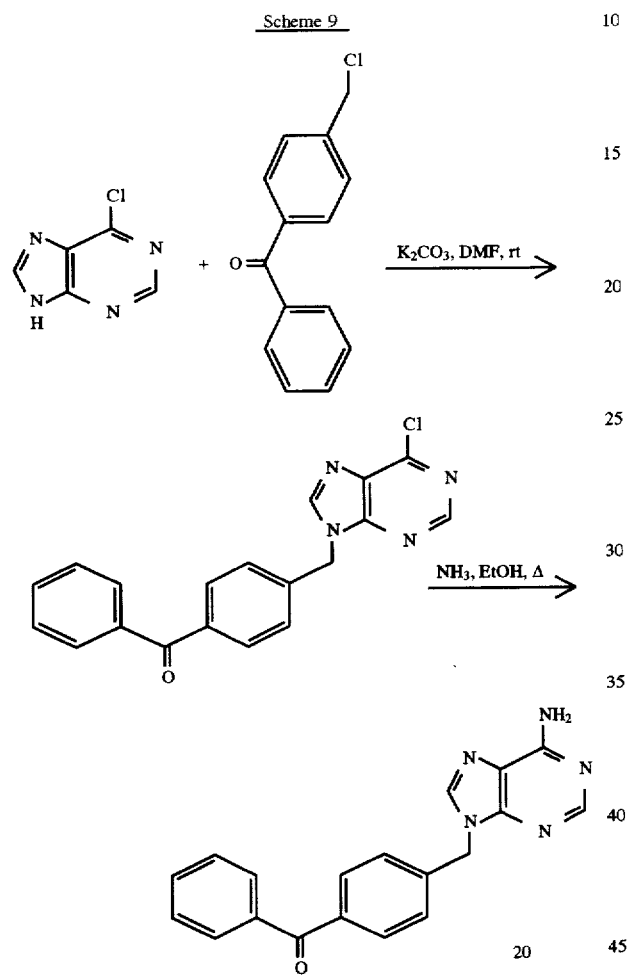

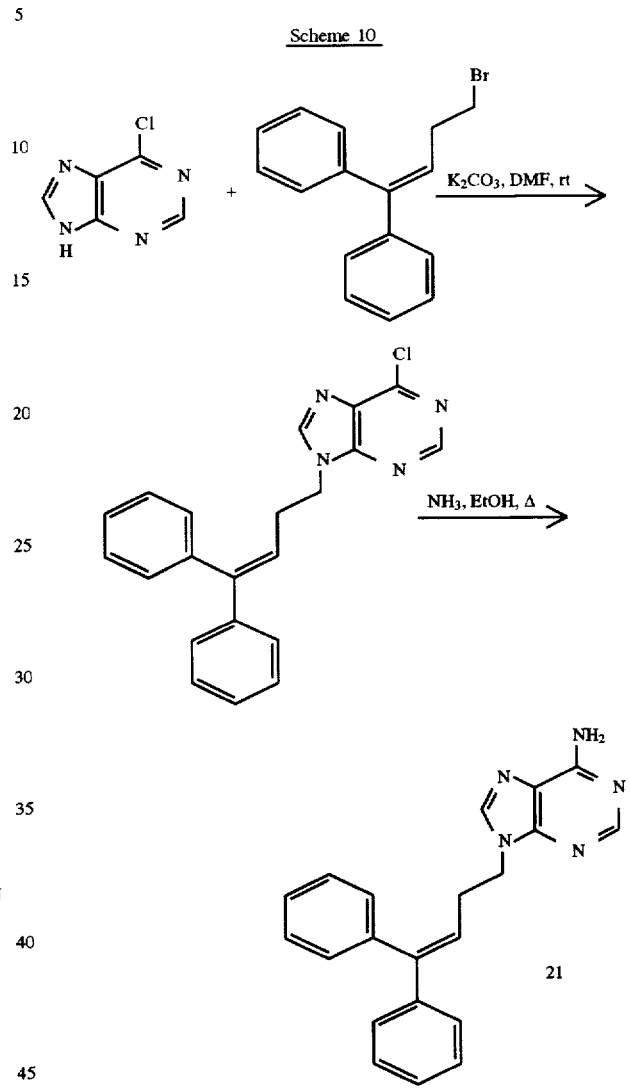

Synthesis of 9-(4-Benzoylbenzyl)-9H-adenine (20)

The synthesis of 9-(4-benzoylbenzyl) -9H-adenine (20) was achieved by the following procedure (Scheme 9). A mixture of 6-chloropurine (3.09 g, 20 mmol), 4-benzoylbenzyl chloride (6.05 g, 22 mmol)and K$_2$CO$_3$ (3.04 g, 22 mmol) in DMF (50 ml) was stirred overnight at rt, diluted with water (400 ml), and extracted with EtOAc (3×100 ml) (Scheme 9)[52]. The combined organic layers were washed with water and brine, dried over MgSO$_4$, concentrated in vacuo, and subjected to flash-chromatography on silica gel eluting with CH$_2$Cl$_2$-acetone (80:20). The fractions containing the higher Rf, the major component, were combined and concentrated in vacuo to give 2.86 g (41%) of 9-(4-benzoylbenzyl)-6-chloro-9H-purine. To a solution of this iminochloride (1.05 g, 3 mmol) in EtOH (20 ml) was added a 2M solution of NH$_3$ in MeOH. This medium was warmed overnight at 90° C. under pressure (constant volume). It was then cooled and concentrated in vacuo. The residue was washed successively with a 1M solution of NaHCO$_3$, water, iPrOH, and hot CH$_2$Cl$_2$, and then was recrystallized from Synthesis of 9-[(4-bis-phenyl)buten-4-yl]-9H-adenine (21)

9-[(4-Bis-phenyl)buten-4-yl]-9H-adenine (21) was synthesized by the following procedure according to Scheme 10. A mixture of 6-chloropurine (2.32 g, 15 mmol), anhydrous K$_2$CO$_3$ (2.21 g, 16 mmol) and [(4-bis-phenyl)buten-4-yl]-bromide (4.31g, 15 mmol) was stirred at ambient temperature for 48 h in DMSO (40ml) (Scheme 10)[53]. The reaction mixture was diluted with 400 ml of cold water and extracted with EtOAc (3×100 ml).

The combined extracts were washed twice with water and once with brine, dried (Na$_2$SO$_4$), and concentrated in vacuo. The crude product was subjected to silica gel chromatography. The column was eluted with EtOAc-Hex, 70:30. The fractions containing the higher R$_f$, the major component, were combined and spin evaporated in vacuo to give 3.42 g (9.48 mmol, 63%) of 6-chloro-9-[(4-bis-phenyl) buten-4-yl] -9H-purine.

A solution of this chloropurine (1.01g, 2.8 mmol) and ammonia (20 mmol) in ethanol was heated at 120° C. for 24 h under pressure (constant volume). The medium was then evaporated in vacuo and the residue was dispersed in 50 ml of a 1M solution of NaHCO₃, extracted with EtOAc, washed with brine, dried over MgSO₄, and purified by flash chromatography on silica gel, eluting with CH₂Cl₂-MeOH, 95:5 yielding 0.55g (1.61 mmol, 58%) of 9-[(4-bis-phenyl)buten-4-yl]-9H-adenine (21). ¹H NMR (CDCl₃) δ 2.69 (dt, 2H, allylic H); 4.26 (t, 2H, CH₂-adenine); 6.01 (t, 1H, vinylic H); 6.13 (br s, 2H, NH₂); 7.08–7.25 (m, 10 H, H—Ph); 7.67 (s, 1H, H-2), 8.28 (s, 1H, H-8)

Scheme 11

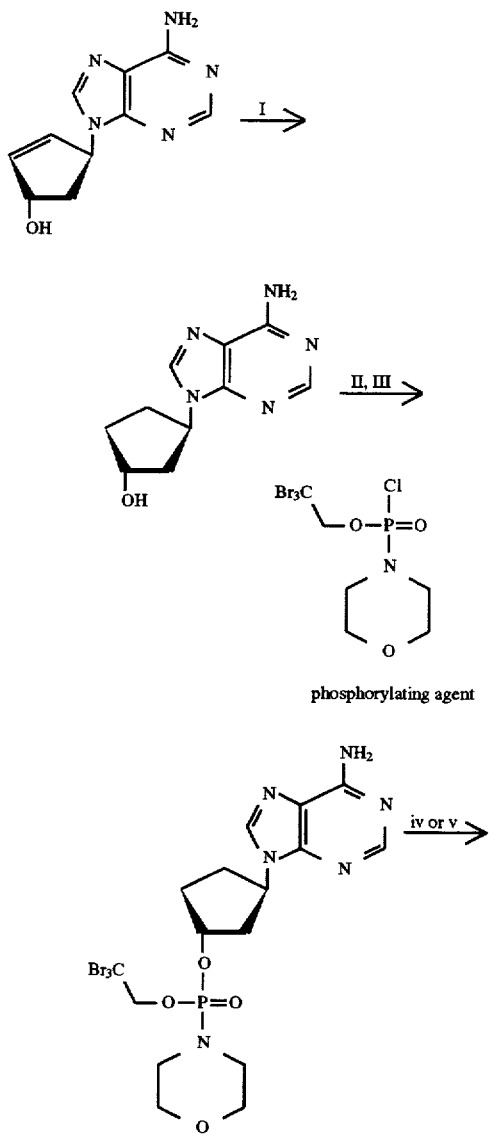

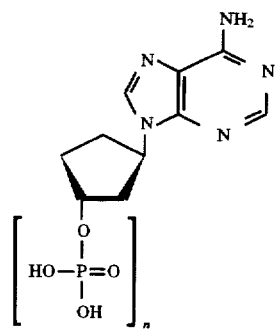

22: n = 1
23: n = 2
24: n = 3

Scheme 11: Reagents and Conditions:
I) H₂Pd/C;
II) tert-BuMgCl, THF, rt;
III) phosphorylating agent, rt;
iv) Zn, pyridine, (Bu₆N)₂H₄P₂O₇ (for 24) or Bu₆N H₃PO₄ (for 23), rt;
v) Zn, DMF followed by 10 mM HCl for 22

The specific reagents and conditions for Scheme 11 are as follows: i, H₂, Pd/C; ii, tert-BuMgCl, THF, rt; iii, phosphorylating agent, rt; iv, Zn, pyridine, (Bu₃N) ₂H₄P₂O₇ (for 24) or BU₃N H₃PO₄ (for 23), rt; v, Zn, DMF followed by 10 mM HCl for 22.

Synthesis of 9-(3-monophosphoryl-cyclopentyl)-adenine (22), 9-(3-diphosphoryl-cyclopentyl)-adenine (23) and 9-(3-triphosphoryl-cyclopentyl)-adenine (24)

The synthesis of this class of compounds proceeds as per scheme 11, with the reagents and conditions given, from 9-(3-hydroxy-cyclopentyl)-adenine. This compound is prepared by hydrogenation of the corresponding cyclopentenyl derivative whose synthesis was described by Dyatkina et al.[54].

Synthesis of 9-[3-(2-O-thiodiphosphoryl) -cyclopentyl] -adenine (25)

The synthesis of 9-[3-(2-O-thiodiphosphoryl)-cyclopentyl]-adenine (25) proceeds from 9-(2-hydroxy-cyclopentyl)-adenine, as per Scheme 5, with the reagents and conditions given.

Synthesis of 9-[3-(3-O-thiotriphosphoryl) -cyclopentyl] -adenine (26)

The synthesis of 9-[3-(2-O-thiotriphosphoryl)-cyclopentyl]-adenine (26) proceeds from compound 23 according to Scheme 6, as above.

Scheme 12

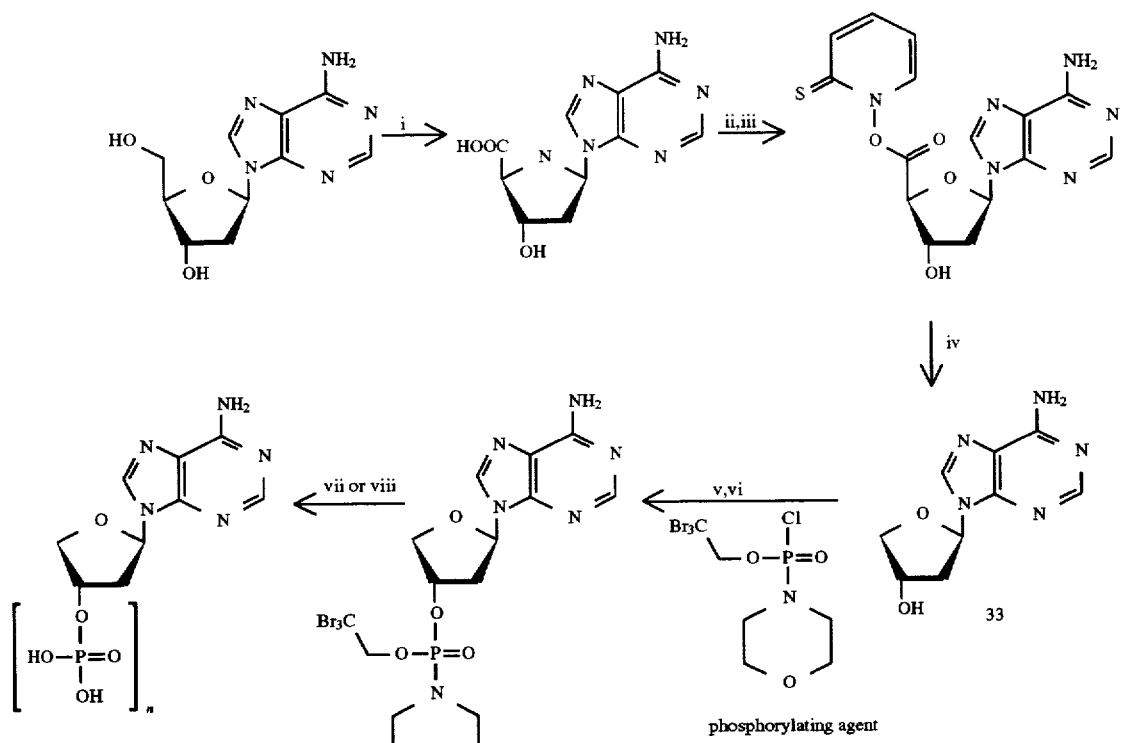

27: n = 1
28: n = 2
29: n = 3

Scheme 12: Reagents and conditions:
i) KMnO₄;
ii) C₂O₂Cl₂;
iii) N-hydroxy-2-pyridinethione, DMAP
iv) Bu₃SnH; v) tert-BuMgCl, THF, rt;;
vi) phosphorylating agent, rt;
vii) Zn, pyridine, (Bu₃N)₂H₄P₂O₇ for 29, or Bu₃N H₃PO₄ for 28, rt;
viii) Zn, DMF, followed by 10 mM HCl for 27.

The specific reagents and conditions for Scheme 12 are as follows: i. KMO₄; ii. C₂O₂Cl₂; iii. N-hydroxy-2-pyridinethione, DMAP; iv. Bu₃SnH; v. tert-BuMgCl, THF, rt; vi. phosphorylating agent, rt; vii. Zn, pyridine, (Bu₃N)₂ H₄P₂O₇ for 29, or BU₃N H₃PO₄ for 28, rt; viii. Zn, DMF, followed by 10 mM HCL for 27.

Synthesis of 9-(tetrahydro-3-monophosphoryl-2-furyl)-adenine (27), 9-(tetrahydro-3-diphosphoryl-2-furyl)-adenine (28) and 9-(tetrahydro-3-triphosphoryl-2-furyl)-adenine (29)

The synthesis of this class of compounds proceeds as per scheme 12, with the reagents and conditions given. The starting nucleoside (33) is synthesized in several steps from 2'-deoxyadenosine (Scheme 12). 2'-Deoxyadenosine is oxidized into an acid according to Wada et al.[55] and decarboxylated by standard procedures[56,57].

Synthesis of 9-[tetrahydro-3-(2-O-thiodiphosphoryl)-2-furyl]-adenine (30)

The synthesis of 9-[tetrahydro-3-(2-O-thiodiphosphoryl)-2-furyl]-adenine (30) proceeds with reagents and conditions according to Scheme 5, above, from compound 33 (Scheme 12).

Synthesis of 9-[tetrahydro-3-(3-0-thiotriphosphoryl)-2-furyl]-adenine (31)

The synthesis of 9-[tetrahydro-3-(3-O-thiotriphosphoryl)-2-furyl]-adenine (31) proceeds with reagents and conditions according to Scheme 6, above, from compound 28 (Scheme 12).

SCHEME 13

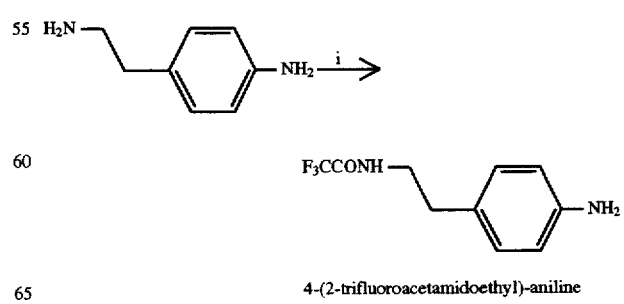

4-(2-trifluoroacetamidoethyl)-aniline

29
-continued
SCHEME 13

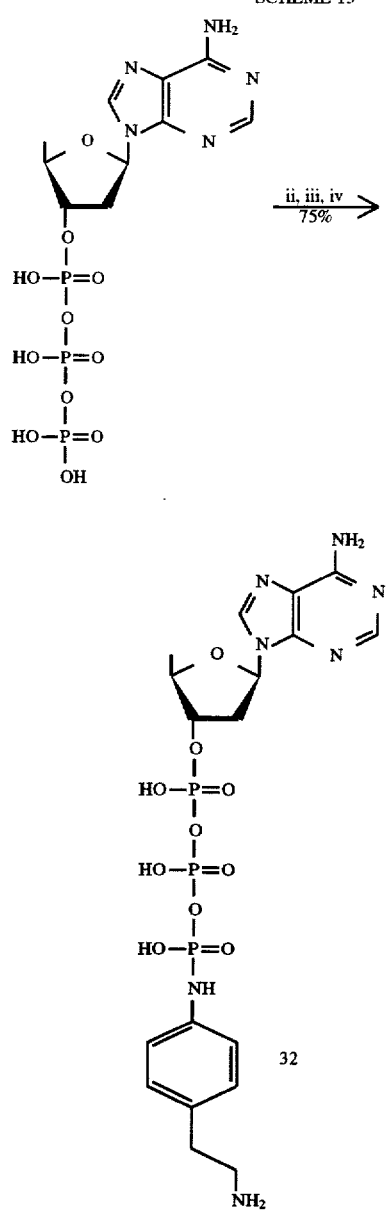

30
-continued
SCHEME 13

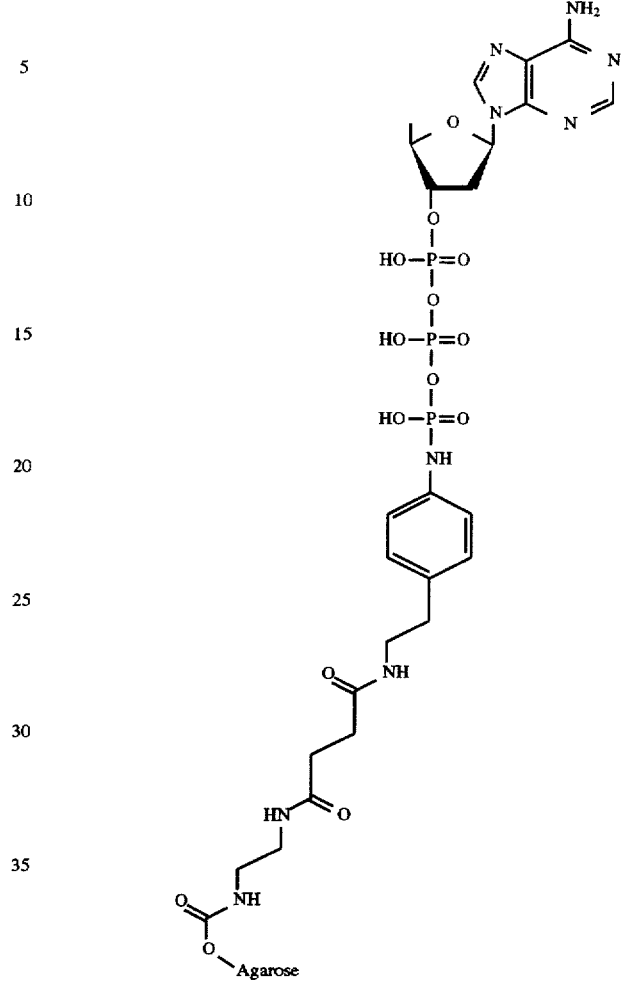

Scheme 13: Reagents and conditions:

i) CF₃COOMe, CHCl₃, 1h;
ii) EDCl, pH 5.6–5.9, H₂O, 3 min;
iii) 4-(2-trifluoroacetamidoethyl)-aniline, pH 6.5, dioxane, 90 min;
iv) NH₃, 6h;
v) Affi-Gel 10, HEPES, MgCl₂, pH 7.5, H₂O, 12h, 4° C.

Synthesis of $P^1$-2', 5'-dideoxyadenosine-3'-$P^3$-4-(2-aminoethyl)-aniline triphosphate (32)

$P^1$-2', 5'-dideoxyadenosine-3 $P^3$-4-(2-aminoethyl)-aniline triphosphate (32) was synthesized by the following procedure according to Scheme 13[43]. Specific reagents and conditions for Scheme 13 are as follows: i, $CF_3COOMe$, $CHCl_3$, 1 h; ii, EDCL, pH 5.6–5.9, $H_2O$, 3 min; iii, 4-(2-trifluoroacetamidoethyl)-aniline, pH 6.5, dioxane, 90 min; iv, $NH_3$, 6 h; v, Affi-Gel 10, HEPES, $MgCl_2$, pH 7.5, $H_2O$, 12 h, 4° C.

Also shown in Scheme 13 is an example of the use of compound 32 in the synthesis of an affinity-chromatography matrix. 1-Ethyl-3-(3-dimethylaminopropyl)-carbodiimide (0.5 g) was added over 3 min to a solution of 0.22 mmol of 2', 5'-dideoxyadenosine-3'-triphosphate (compound 4) in 10 mL of water while the pH was maintained between 5.6 and 5.9 by the dropwise addition of a 0.2N HCl solution (Scheme 13). After 10 min 6 mL of a solution of 0.46 g (2 mmol) of (2-trifluoroacetamidoethyl)-aniline in dioxane was added. The pH was adjusted to 6.5. The reaction was left at room temperature for 90 min and then it was cooled to 5° C. in an ice-water bath. Ammonia was bubbled through the mixture for 20 min and it was left at room temperature for 6 h. The deprotected adduct was purified by anion exchange chromatography on QAE Sephadex, eluting the product with a gradient of $Et_3N.H_2CO_3$ to afford 0.165 mmol of adduct (32) (75%). Trisodium salt: $^1H$ NMR (250 MHz, $D_2O$) δ 1.13 (d, 3H, J×6.6 Hz, 3H-5'), 2.11 (t, 2H, J=7.2 Hz, $CH_2$), 2.37–2.48 (m, 4H, H-2', H-2" and $CH_2$), 4.14–4.18 (m, 1H, H-4'), 4.55–4.60 (m, 1H, H-3'), 5.99 (t, 1H, J=7.2 Hz), 6.70 (dd, 4H, J=8.5 Hz, J=31 Hz, H-aryl), 8.08 (s, 1H, H-2), 8.14 (s, 1H, H-8). $^{31}P$ NMR (100 MHz, $D_2O$) δ —18.26 (dd, J=18.6 Hz, P-2), -8.05 (dd, $J_{P-H}$=7.9 Hz, $J_{P-P}$=8.4 Hz, P-1), -5.64 (d, J=18.8 Hz, P-3)

Synthesis of adenosine-3'-di-and -3'-triphosphates

Adenosine-3'-diphosphate (34) and adenosine-3'-triphosphate (35) were prepared according to procedures described elsewhere [31].

Determination of adenylyl cyclase activity

Detergent-dispersed adenylyl cyclase from rat brain was prepared as previously described[58]. Activities were determined in a reaction mixture containing 50 mM N-[2-hydroxyethyl]-piperazine-N'-[2-ethanesulfonic acid] (HEPES) or 50 mM triethanolamine•HCl, pH 7.5, 5 mM $MnCl_2$, 100 μM 5'ATP, [α-$^{32}$p]5'ATP (ca. 2 to 5×10$^5$ dpm), 0.1% (w/v) Lubrol-PX, 1 mM 3-isobutyl-1-methylxanthine, 1 mM dithiothreitol, 1 mg bovine serum albumin per ml, 2 mM creatine phosphate, 100 μg creatine kinase per ml, and 100 μM forskolin, in a reaction volume of 100 μl. Reactions were for 15 min at 30° C. and were terminated by the addition of 0.6 ml 120 mM zinc acetate containing 0.5 mM cAMP and 0.5 ml 144 mM sodium carbonate as described by Jakobs et al.[59].

The resulting $ZnCO_3$ precipitate was sedimented by centrifugation in a desktop microfuge. The [$^{32}$P] cAMP in the supernatant fraction was then purified free of residual substrate and other contaminants by sequential chromatography on Dowex-50 and $Al_2O_3$, as described by Salomon et al.[60]. [$^{32}$P]cAMP was quantified by Cherenkov radiation in a liquid scintillation spectrometer.

The synthesized adenine derivatives, 1–5, 8, 11–13, 16, 19–21, 34 and 35 were each tested separately in vitro for their ability to inhibit adenylyl cyclase activity by administration of each compound to the above-described adenylyl cyclase assay. The results for some of these compounds are shown in Table I.

TABLE I

IC$_{50}$ values for inhibition of rat brain adenylyl cyclase by adenine nucleosides and 3'-phosphorylated derivatives.

| Nucleoside | IC$_{50}$ (μM) | n | X | Y | Z |
|---|---|---|---|---|---|
| adenosine | 82* | 0 | OH | OH | — |
| 3'AMP | 8.9 | 1 | OH | OH | OH |
| 3'ADP (34) | 3.9 | 2 | OH | OH | OH |
| 3'ATP (35) | 2.0 | 3 | OH | OH | OH |
| 2'-deoxyadenosine | 15* | 0 | OH | H | — |
| 2'd3'AMP | 1.2* | 1 | OH | H | OH |
| 2'd3'ADP (11) | 0.14 | 2 | OH | H | OH |
| 2'd3'ATP (12) | 0.090 | 3 | OH | H | OH |
| 2'd3'A4P (13) | 0.013 | 4 | OH | H | OH |
| 2',5'-dideoxyadenosine | 2.7* | 0 | H | H | OH |
| 2'5'dd3'AMP | 0.46 | 1 | H | H | OH |
| 2',5'dd3'ADP (3) | 0.10 | 2 | H | H | OH |
| 2',5'dd3'ATP (4) | 0.040 | 3 | H | H | OH |
| 2',5'dd3'A$_4$P (5) | 0.010 | 4 | H | H | OH |
| 2'5'dd3'AMP-dansyl (1) | 3.0 | 1 | H | H | dansyl |
| 2'5'dd3'AMP-chol (2) | >300 | 1 | H | H | cholesteryl |

*Values from Johnson, R.A., Yeung, S.-M.H., Stubner, D., Bushfield, M., and Shoshani, I. (1989) Molec. Pharmacol. 35: 681–688[19].

In the results presented in Table I, the naturally occurring adenosine was used as a positive control and yielded a IC$_{50}$ of 82 μM. In contrast, each of synthesized compounds 1, 3–5 and 11–13 inhibited adenylyl cyclase activity at concentrations considerably lower than that for adenosine. Compounds 8, 16 and 19 also inhibited adenylyl cyclase activity at concentrations considerably lower than that for adenosine. Effects of 3'ADP (34) and 3'ATP (35) are shown for comparison. Only compound 2 was less effective than adenosine in the inhibition of adenylyl cyclase activity. Results with previously known 3'-adenosine derivatives are included for comparison purposes. It should be noted that the series of 2', 5'-dideoxyadenosine-3'-polyphosphates include far and away the most potent in vitro inhibitors of adenylyl cyclase activity that are more potent than many hormones whose effects must be mediated by G-proteins.

It is important to note that all known mammalian adenylyl cyclases, except possibly the membrane-bound form from sperm[61] and the putative soluble form from testis, are inhibited by this class of compounds via a distinct domain. Hence, inhibition is not dependent on tissue source. Furthermore, inhibition occurs with membrane-bound enzyme, enzyme extracted from membranes by detergent, purified enzyme, and recombinant expressed enzyme, though potency of inhibition is less with the purified and recombinant forms of the enzyme (Table II).

TABLE II

IC$_{50}$ values for inhibition of different adenylyl cyclases by 2', 5'-dideoxyadenosine 3'-polyphosphates.

| Enzyme Source | 2',5'dd3'AMP | 2',5'dd3'ADP(3) (nM) | 2',5'dd3'ATP(4) |
|---|---|---|---|
| Rat brain, detergent extract$^a$ | 460 | 100 | 40 |
| Bovine brain, purified$^b$ | nd | 560 | 120 |

TABLE II-continued

IC$_{50}$ values for inhibition of different adenylyl cyclases by 2', 5'-dideoxyadenosine 3'-polyphosphates.

| Enzyme Source | 2',5'dd3'AMP | 2',5'dd3'ADP(3) (nM) | 2',5'dd3'ATP(4) |
|---|---|---|---|
| Type I, purified recombinant[c] | 1990 | 250 | 170 |

[a]Values from Table I
[b]Forskolin eluates from forskolin-affinity column as per |[62]|
[c]Forskolin eluate as per |[63]|
nd - not determined

References

The following scientific articles have been cited throughout this application.

1. Sunahara, R. K., Dessauer, C. W., and Gilman, A. G. Annu. Rev. Toxicol. 36: 461–480.
2. Beavo, J .A.; Reisfsnyder, D. D. Trends Pharmacol. Sci. 11: 150, 1990.
3. Murray, K. J., and Warrington, B. H., In: *Comprehensive Medicinal Chemistry*. (Sammes P. G., Ed.); Pergamon, Vol. 2, Chapter 8.7., pp 531, 1990.
4. Murray, K. J., and England, P. J., Biochem. Soc. Trans. 20: 460–464, 1992.
5. Serafin, W. E., Drugs used in the treatment of Asthma, In: *Goodman & Gilman's The Pharmacological Basis of Therapeutics*, (Hardman, J. G., Limbird, L. E., Molinoff, P. B., Ruddon, R. W., and Gilman, A. G., Eds.) Ninth Edition, Chapter 28, pp. 659–682, McGraw-Hill, New York, 1996.
6. Eckmann, R., Fichte, K., Meya, U., and Sastre-Y-Hernandez, M., Curr. Ther. Res. 43: 291–295, 1987.
7. Hoffman, B. B., and Lefkowitz, R. J., Catecholamines, sympathomimetic drugs, and adrenergic receptor antagonists, In: *Goodman & Gilman's The Pharmacological Basis of Therapeutics*, (Hardman, J. G., Limbird, L. E., Molinoff, P. B., Ruddon, R. W., and Gilman, A. G., Eds.) Ninth Edition, Chapter 10, pp. 199–248, McGraw-Hill, New York, 1996.
8. Johnson, R. A., Yeung S.-M. H., Bushfield, M., Stübner,D., and Shoshani, I. In: *Role of adenosine and adenine nucleotides in the biological systems*, (Imai, S., and Nakazawa, M., Eds.); Elsevier: Amsterdam, pp 43–55, 1990.
9. Londos, C., and Wolff, J., Proc. Natl. Acad. Sci. USA 74: 5482–5486, 1977.
10. Weinryb, I., and Michel, L M., Biochim. Biophys. Acta 334: 218–225, 1974.
11. Sahyoun, N., Schmitges, C. J., Siegel, M. I., and Cuatrecasas, P., Life Sci. 19: 1971–1980, 1977.
12. Johnson, R. A., and Welden, J., Arch. Biochem. Biophys. 183: 216–227, 1977.
13. Londos, C., and Preston, M. S., J. Biol. Chem. 252: 5951–5956, 1977.
14. Johnson, R. A., Saur, W., and Jakobs, K. H., J. Biol. Chem. 254: 1094–1101, 1979.
15. Yeager, R. E., Nelson, R., and Storm, D. R., J. Neurochem. 47: 139–144, 1986.
16. Johnson, R. A., and Shoshani, I., J. Biol. Chem. 265: 11595–11600, 1990.
17. Yeung, S. M. H., and Johnson, R. A., J. Biol. Chem. 265: 16745–16750, 1990.
18. Florio, V. A., and Ross, E. M., Molec. Pharmacol. 24: 195–202, 1983.
19. Johnson, R. A., Yeung, S.-M. H., Stübner, D., Bushfield, M., and Shoshani, I., Molec. Pharmacol. 35: 681–688, 1989.
20. Stübner, D., and Johnson, R. A., FEBS Lett. 248: 155–161, 1989.
21. Bushfield, M., Shoshani, I., and Johnson, R. A., Molec. Pharmacol. 38: 848–853, 1990.
22. Lyons, E., Jr., Shoshani, I., Iyengar, R., and Johnson, R. A., Fed. Proc. 8(7): A1418, 1994.
23. Nimit, Y., Law, J., and Daly, J. W., Biochem. Pharmacol. 31: 3279–3287, 1982.
24. Soechtig, E., and Trost, T., Pharmacology 23: 82–90, 1981.
25. Simoncsits, A., and Tomasz, J., Biochim. Biophys. Acta 340: 509–515, 1974.
26. Kozarich, J. W., Chinault, A. C., and Hecht, S. M., Biochemistry 14: 981, 1975.
27. Hamel, E., Heimer, E. P., and Nussbaum, A. L., Biochemistry 14: 5055, 1975.
28. Bennett, G. N., Gough, G. R., and Gilham, P. T., Biochemistry 15: 4623, 1976.
29. Schattenkerk, Wreesmann, C. T. J., van der Marel, G. A., and van Boom, J. H., Nucl. Acids Res. 13: 3635, 1985.
30. Josse, J., and Moffatt, J. G., Biochemistry 4: 2825–2831, 1965.
31. Mitchel, R. E. J., Ward, D. C., and Tener, G. M., Can. J. Biochem. 45: 89, 1967.
32. den Hartog, J. A. J., Lawson, M. P., de Jong, E. W. P., and van Boom, J. H., Recl. Trav. Chim. Pays-Bas 100: 317, 1981.
33. Schattenkerk, C., Visser, G. M., van der Marel, G. A., and van Boom, J. H., Nucl. Acids Res. 11: 7545, 1983.
34. Cashel, M., and Gallant, J. Nature (London) 221: 838, 1969.
35. Cashel, M. J. Biol. Chem. 244: 3133, 1969.
36. Sy, J., and Lipmann, F. Proc. Natl. Acad. Sci. USA 70: 306, 1973.
37. Sy, J., Ogawa, Y., and Lipmann, F. Proc. Natl. Acad. Sci. USA 70: 2145, 1973.
38. Haseltine, W. R., and Block, R. Proc. Natl. Acad. Sci. USA 70: 1564, 1973.
39. Zenser, T. V., and Wannemachere, R. W., Jr., Proc. Soc. Exp. Biol. & Med., 152: 126–129, 1976.
40. Désaubry, L., Shoshani, I., and Johnson, R. A., Nucleosides and Nucleotides 14(6): 1453–1460, 1995.
41. Désaubry, L., Shoshani, I., and Johnson, R. A., Tetrahedron Letters 36(7): 995–996, 1995.
42. Désaubry, L., Shoshani, I, and Johnson, R. A., J. Biol. Chem. 271: 14028–14034, 1996.
43. Désaubry, L., and Johnson, R. A., Bioorg. Med. Chem. (In Press), 1997.
44. Ti, G. S., Gaffney, B. L., and Jones, R. A., J. Am. Chem. Soc. 104: 1316, 1982.
45. van Boom, J. H., Burgers, P. M. J., van der Marel, G. A., Verdegaal, C. H. M., and Wille, G., Nucleic Acids Res. 4: 1047, 1977.
46. Yamasaki, T., Sato, T., Science Repts. Res. Inst. Tohoku Univ., Ser. A, 6: 384–389, 1954.
47. Burgers, P. M. J., and Eckstein, F., Biochemistrey 18: 592–596, 1979.
48. Goody, R. S., and Eckstein, F., J. Am Chem. Soc., 93: 6252–6257, 1971.
49. Burgers, P. M., and Eckstein, F. Biochemistry. 18(4): 592–596, 1979
50. Burgers, P. M. J., Eckstein, F., Tetrahedron Lett. 40: 3835–3838, 1978.
51. Beaman, A. G., and Robins, R. K. J. Org. Chem. 28: 2310–2313, 1963.

52. Itoh, T. and Hall, H. K., Jr. *Macromolecules* 23: 4879–4881, 1990.
53. N' Goka V., Schlewer, G., Linget, J. M., Chambon, J. P., Wermuth, CG., *J. Med. Chem.* 34: 2547–2457, 1991.
54. Dyatkina, N., Theil, F., Ballschuh, S., von JantaLipinski, M., *Tetrahedron*, 51: 761, 1995.
55. Wada, T., Minamimoto, N., Okada, K., Miyabayashi, K., Inaki,Y., Miyata, M., (22$^{nd}$ *Symposium on Nucleic Acids Chemistry*, 1995), *Nucleic Acids Symp.* Ser. 34: 189–190, 1995.
56. Barton, D. H. R., Gero, S. D., Quiclet-Sire, B., Samadi, M., *J. Chem. Soc., Chem. Commun.* 15: 1000–1001, 1989.
57. Barton, D. H. R., Zard, S. Z., *Pure & Appl. Chem.*, 58:675–684, 1986.
58. Johnson, R. A., and Sutherland, E. W., *Methods in Enzymol.* 38: 135–143, 1973.
59. Jakobs, K. H., Saur, W., and Schultz, G., *J. Cyclic Nucleotide Res.* 2: 381–392, 1976.
60. Salomon, Y., Londos, C., and Rodbell, M., *Anal. Biochem.* 58: 541–548, 1974.
61. Johnson, R. A., and Shoshani, I. *J. Siol. Chem.* 265: 19035–19039, 1990.
62. Pfeuffer, E., Mollner, S., and Pfeuffer, T., *EMBO J.* 4: 3675–3679, 1985.
63. Taussig, R., Quarmby, L. M., and Gilman, A. G., *J. Biol. Chem.* 268: 9–12, 1993.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All scientific articles cited herein are hereby incorporated by reference in their entirety and relied upon.

What is claimed is:

1. A method for the determination of inhibition of adenylyl cyclase activity, comprising the steps of:
   a) adding an adenine-or 3'-adenosine derivative to a cell extract containing adenylyl cyclase and expressing adenylyl cyclase activity;
   b) allowing the adenine-or 3'-adenosine derivative to react with the adenylyl cyclase; and
   c) determining the amount of inhibition of adenylyl cyclase activity, wherein the adenine-or 3'-adenosine derivatives is selected from the group consisting of:
   1) 2', 5'-dideoxyadenosine-3'-[2-([(5-dimethylamino-1-naphthalenesulfonamido)-(N-methyl)]-aminoethyl)-phosphate];
   2) 2', 5'dideoxyadenosine-3'-[(3-cholesteryl)-phosphate];
   5) 2', 5'-dideoxyadenosine-3'-tetraphosphate;
   6) 2', 5'-dideoxyadenosine-3'-(($\beta\gamma$-imino-triphosphate);
   7) 2', 5'-dideoxyadenosine-3'-($\beta\gamma$-methylene-triphosphate);
   8) 2', 5'-dideoxyadenosine-3'-O-thiophosphate;
   9) 2', 5'-dideoxyadenosine-3'-(2-O-thiodiphosphate);
   10) 2', 5'-dideoxyadenosine-3'-(3-O-thiotriphosphate);
   11) 2'-deoxyadenosine-3'-diphosphate;
   12) 2'-deoxyadenosine-3'-triphosphate;
   13) 2'-deoxyadenosine-3'-tetraphosphate;
   14) 2'-deoxyadenosine-3'-($\beta\gamma$-imino-triphosphate);
   15) 2'-deoxyadenosine-3'-($\beta\gamma$-methylene-triphosphate);
   16) 2'-deoxyadenosine-3'-O-thiophosphate;
   17) 2'-deoxyadenosine-3'-(2-O-thiodiphosphate);
   18) 2'-deoxyadenosine-3'-(3-O-thiotriphosphate);
   27) 9-(tetrahydro-3-monophosphoryl-2-furyl)-adenine;
   28) 9-(tetrahydro-3-diphosphoryl-2-furyl)-adenine;
   29) 9-(tetrahydro-3-triphosphoryl-2-furyl)-adenine;
   30) 9-[tetrahydro-3-(2-O-thiodiphosphoryl)-2-furyl]-adenine;
   31) 9-[tetrahydro-3-(3-O-thiotriphosphoryl)-2-furyl]-adenine;
   34) adenosine-3'-diphosphate; and
   35) adenosine-3'-triphosphate.

2. A compound, wherein said compound is a 3'-adenosine derivative selected from the group consisting of:
   1) 2', 5'-dideoxyadenosine-3'-[2-([(5-dimethylamino-1-naphthalenesulfonamido)-(N-methyl)]-aminoethyl)-phosphate];
   2) 2', 5'dideoxyadenosine-3'-[(3-cholesteryl)-phosphate];
   5) 2', 5'-dideoxyadenosine-3'-tetraphosphate;
   6) 2', 5'-dideoxyadenosine-3'-($\beta\gamma$-imino-triphosphate);
   7) 2', 5'-dideoxyadenosine-3'-($\beta\gamma$-methylene-triphosphate);
   8) 2', 5'-dideoxyadenosine-3'-O-thiophosphate;
   9) 2', 5'-dideoxyadenosine-3'-(2-O-thiodiphosphate);
   10) 2', 5'-dideoxyadenosine-3'-(3-O-thiotriphosphate);
   13) 2'-deoxyadenosine-3'-tetraphosphate;
   14) 2'-deoxyadenosine-3'-($\beta\gamma$-imino-triphosphate);
   15) 2'-deoxyadenosine-3'-($\beta\gamma$-methylene-triphosphate);
   16) 2'-deoxyadenosine-3'-O-thiophosphate;
   17) 2'-deoxyadenosine-3'-(2-O-thiodiphosphate);
   18) 2'-deoxyadenosine-3'-(3-O-thiotriphosphate);
   27) 9-(tetrahydro-3-monophosphoryl-2-furyl)-adenine;
   28) 9-(tetrahydro-3-diphosphoryl-2-furyl)-adenine;
   29) 9-(tetrahydro-3-triphosphoryl-2-furyl)-adenine;
   30) 9-[tetrahydro-3-(2-O-thiodiphosphoryl)-2-furyl]-adenine;
   31) 9-[tetrahydro-3-(3-O-thiotriphosphoryl)-2-furyl]-adenine; and
   32) P$^1$-2', 5'-dideoxyadenosine-3'-P$^3$-4-(2-aminoethyl)-aniline triphosphate.

3. The compound of claim 2, wherein the 3'-adenosine derivative is 2', 5'dideoxyadenosine-3'-[(3-cholesteryl)-phosphate] (2), having the structural formula:

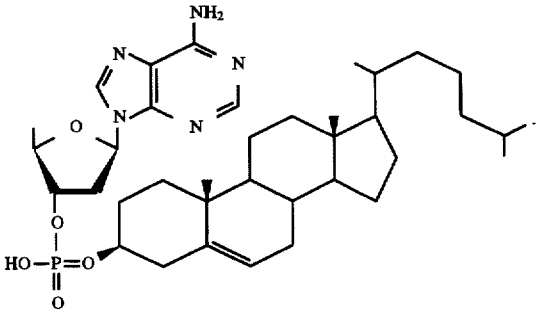

4. The compound of claim 2, wherein the 3'-adenosine derivative is 2', 5'-dideoxyadenosine-3'-[2-([(5-dimethylamino-1-naphthalenesulfonamido) -(N-methyl)]- aminoethyl)-phosphate [(1), having the structural formula:

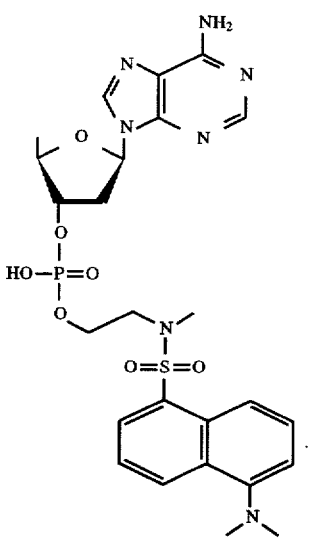

5. The compound of claim 2, wherein the 3'-adenosine derivative is P$^1$-2', 5'-dideoxyadenosine-3'-P$^3$-4-(2-aminoethyl)-aniline triphosphate (32), having the structural formula:

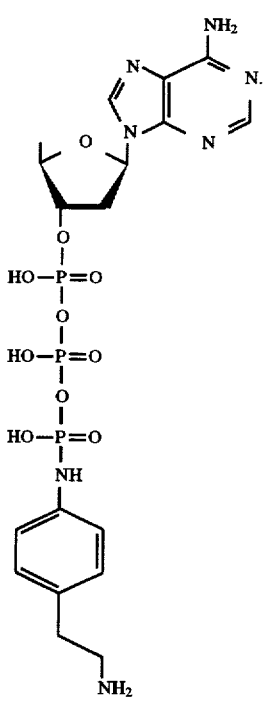

6. The compound of claim 2, wherein the 3'-adenosine derivative is 2', 5'-dideoxyadenosine-3'-tetraphosphate (5), having the structural formula:

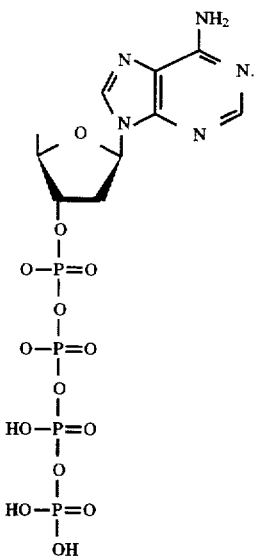

7. The compound of claim 2, wherein the 3'-adenosine derivative is 2', 5'-dideoxyadenosine-3'-(βγ-imino-triphosphate (6), having the structural formula:

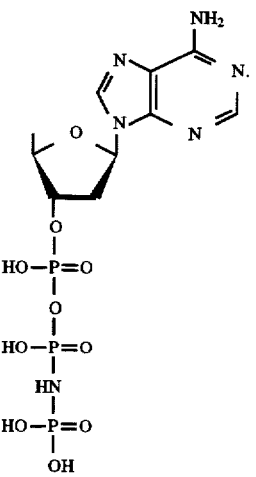

8. The compound of claim 2, wherein the 3'-adenosine derivative is 2', 5'-dideoxyadenosine-3'-(βγ-methylene-triphosphate (7), having the structural formula:

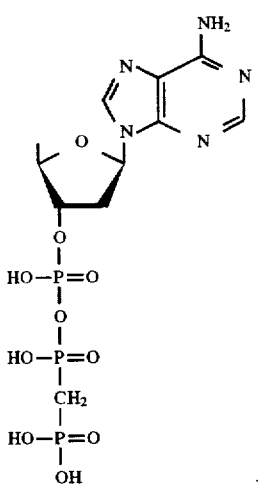

9. The compound of claim 2, wherein the 3'-adenosine derivative is 2', 5'-dideoxyadenosine-3'-O-thiophosphate (8), having the structural formula:

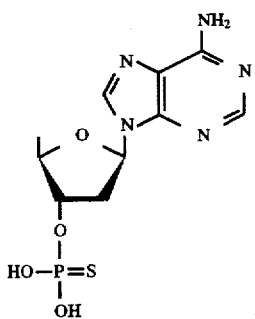

10. The compound of claim 2, wherein the 3'-adenosine derivative is 2', 5'-dideoxyadenosine-3'-(2-O-thiodiphosphate (9), having the structural formula:

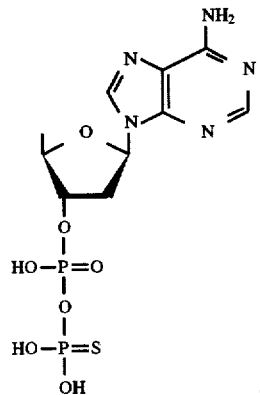

11. The compound of claim 2, wherein the 3'-adenosine derivative is 2', 5'-dideoxyadenosine-3'-(3-O-thiotriphosphate (10), having the structural formula:

12. The compound of claim 2, wherein the 3'-adenosine derivative is 9-[tetrahydro-3-(2-O-thiodiphosphoryl)-2-furyl]-adenine (30), having the structural formula:

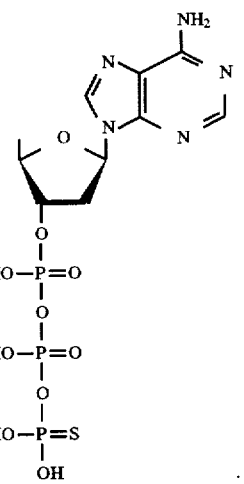

13. The compound of claim 2, wherein the 3'-adenosine derivative is 9-[tetrahydro-3-(3-0-thiotriphosphoryl)-2-furyl]-adenine (31), having the structural formula:

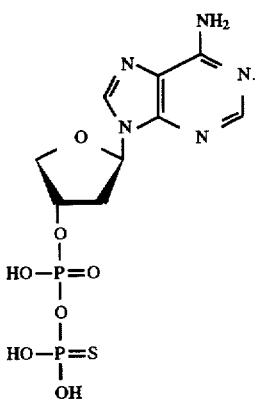

14. The compound of claim 2, wherein the 3'-adenosine derivative is 2'-deoxyadenosine-3'-tetraphosphate (13), having the structural formula:

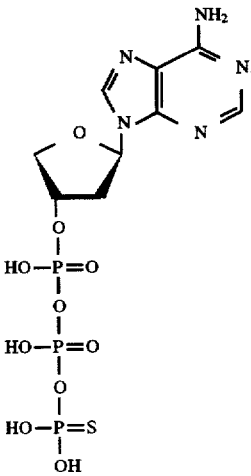

15. The compound of claim 2, wherein the 3'-adenosine derivative is 2'-deoxyadenosine-3'-(βγ-imino-triphosphate) (14), having the structural formula:

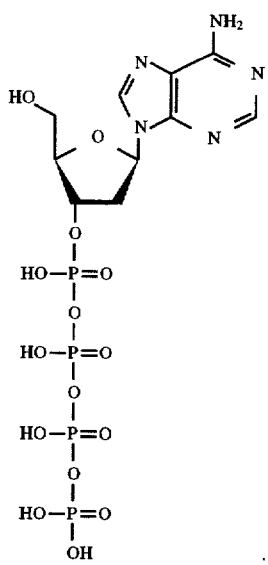

16. The compound of claim 2, wherein the 3'-adenosine derivative is 2'-deoxyadenosine-3'-βγ-methylene-triphosphate (15), having the structural formula:

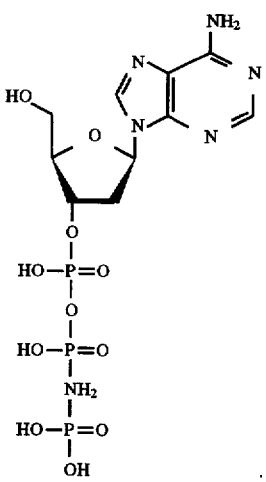

17. The compound of claim 2, wherein the 3'-adenosine derivative is 2'-deoxyadenosine-3'-O-thiophosphate (16), having the structural formula:

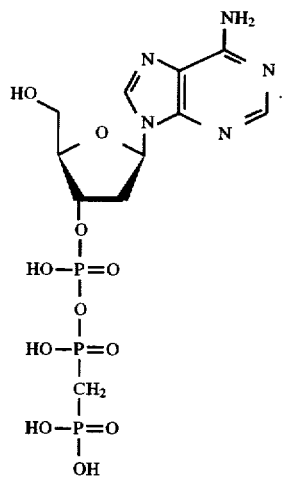

18. The compound of claim 2, wherein the 3'-adenosine derivative is 2'-deoxyadenosine-3'-(2-O-thiodiphosphate) (17), having the structural formula:

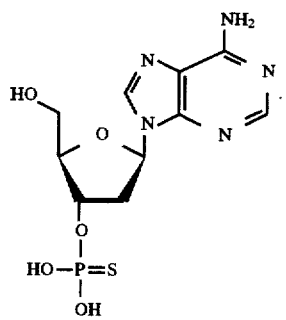

19. The compound of claim 2, wherein the 3'-adenosine derivative is 2'-deoxyadenosine-3'-(3-O-thiotriphosphate) (18), having the structural formula:

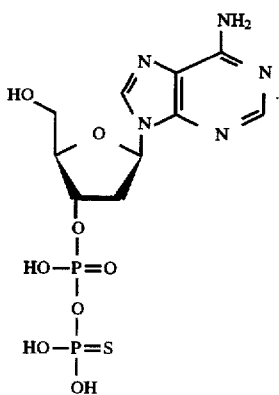

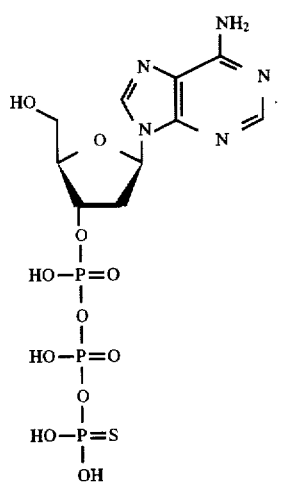

20. The compound of claim 2, wherein the 3'-adenosine derivative is 9-(tetrahydro-3-monophosphoryl-2-furyl)-adenine (27) having the structural formula:

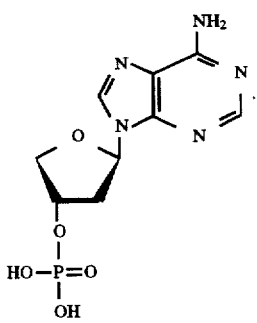

21. The compound of claim 2, wherein the 3'-adenosine derivative is 9-(tetrahydro-3-diphosphoryl-2-furyl)-adenine (28) having the structural formula:

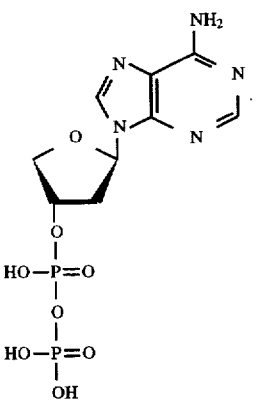

22. The compound of claim 2, wherein the 3'-adenosine derivative is 9-(tetrahydro-3-triphosphoryl-2-furyl)-adenine (29) having the structural formula:

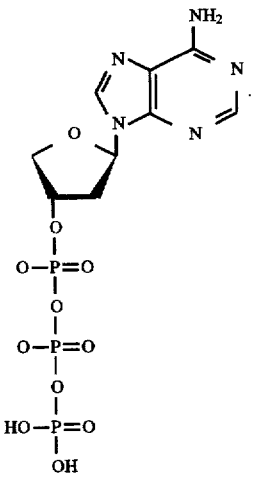

* * * * *